US012576388B2

(12) United States Patent
Mitsukami et al.

(10) Patent No.: US 12,576,388 B2
(45) Date of Patent: Mar. 17, 2026

(54) WATER ABSORBING AGENT COMPOSITION AND METHOD FOR PRODUCING SAME

(71) Applicant: NIPPON SHOKUBAI CO., LTD., Osaka (JP)

(72) Inventors: Yoshiro Mitsukami, Himeji (JP); Tatsuya Yamaguchi, Himeji (JP); Takaaki Wada, Suita (JP); Setsu Inoue, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 636 days.

(21) Appl. No.: 18/013,048

(22) PCT Filed: Jul. 13, 2021

(86) PCT No.: PCT/JP2021/026205
§ 371 (c)(1),
(2) Date: Dec. 27, 2022

(87) PCT Pub. No.: WO2022/014550
PCT Pub. Date: Jan. 20, 2022

(65) Prior Publication Data
US 2023/0285935 A1 Sep. 14, 2023

(30) Foreign Application Priority Data

Jul. 13, 2020 (JP) ................................. 2020-120248

(51) Int. Cl.
| | |
|---|---|
| *B01J 20/26* | (2006.01) |
| *A61L 15/18* | (2006.01) |
| *A61L 15/22* | (2006.01) |
| *A61L 15/60* | (2006.01) |
| *B01J 20/04* | (2006.01) |
| *B01J 20/24* | (2006.01) |
| *B01J 20/30* | (2006.01) |

(52) U.S. Cl.
CPC ............. *B01J 20/267* (2013.01); *A61L 15/18* (2013.01); *A61L 15/225* (2013.01); *A61L 15/60* (2013.01); *B01J 20/045* (2013.01); *B01J 20/24* (2013.01); *B01J 20/3021* (2013.01); *B01J 20/3085* (2013.01)

(58) Field of Classification Search
CPC ...... B01J 20/045; B01J 20/261; B01J 20/267; B01J 20/3021; B01J 20/3085; B01J 20/24; B01J 2220/68; A61L 15/18; A61L 15/60; A61L 15/225; C08L 33/02; C08L 3/06; C08F 8/00; C08F 220/06; C08F 220/303; C08F 2810/20; C08F 222/1063

USPC ...................................... 252/194, 181.1, 408
See application file for complete search history.

(56) References Cited

U.S. PATENT DOCUMENTS

| | | | |
|---|---|---|---|
| 4,076,663 A | 2/1978 | Masuda et al. | |
| 4,863,989 A | 9/1989 | Obayashi et al. | |
| 4,972,019 A | 11/1990 | Obayashi et al. | |
| 5,340,853 A | 8/1994 | Chmelir et al. | |
| 5,733,576 A | 3/1998 | Chmelir | |
| 2005/0085604 A1 | 4/2005 | Handa et al. | |
| 2006/0074160 A1 | 4/2006 | Handa et al. | |
| 2007/0111004 A1 | 5/2007 | Handa et al. | |
| 2007/0239124 A1 | 10/2007 | Handa et al. | |
| 2008/0177057 A1 | 7/2008 | Bolduc et al. | |
| 2010/0057027 A1 | 3/2010 | Furno et al. | |
| 2011/0313113 A1 | 12/2011 | Sakamoto et al. | |
| 2012/0258851 A1 | 10/2012 | Nakatsuru et al. | |
| 2013/0026412 A1 | 1/2013 | Machida et al. | |
| 2013/0101851 A1 | 4/2013 | Takaai et al. | |
| 2013/0264517 A1 | 10/2013 | Matsumoto et al. | |
| 2013/0296548 A1 | 11/2013 | Godin et al. | |
| 2014/0296465 A1 | 10/2014 | Sakamoto et al. | |
| 2014/0299815 A1 | 10/2014 | Ueda et al. | |
| 2014/0339469 A1 | 11/2014 | Furno et al. | |

(Continued)

FOREIGN PATENT DOCUMENTS

| | | |
|---|---|---|
| CN | 102574100 A | 7/2012 |
| CN | 103261243 A | 8/2013 |

(Continued)

OTHER PUBLICATIONS

Sumiya et al., JP 1992/120111 (04-120111) Machine Translation, Apr. 21, 1992 (Year: 1992).*

(Continued)

*Primary Examiner* — Jessica Whiteley
(74) *Attorney, Agent, or Firm* — Harness Dickey & Pierce P.L.C.

(57) ABSTRACT

Provided are a water-absorbing agent composition of high quality (and stable quality) that can be produced without a decrease in productivity and is not colored even in a production process (or under production conditions) under high temperature conditions (under the condition of heating at 100° C. or higher), even when a polysaccharide is used as a sustainable raw material for at least part of the water-absorbing agent composition, and a method for producing the water-absorbing agent composition. The water-absorbing agent composition includes: a polyacrylic acid (salt)-based water-absorbing resin; a polysaccharide, and a reducing agent. The water-absorbing agent composition is surface-crosslinked, contains the polysaccharide in an amount of 10 mass % or more and contains the reducing agent in an amount of 10 ppm to 10000 ppm, and has a degree of coloration (YI value) of 60 or less.

14 Claims, No Drawings

(56) References Cited

U.S. PATENT DOCUMENTS

| | | |
|---|---|---|
| 2015/0259494 A1 | 9/2015 | Takaai et al. |
| 2016/0332141 A1 | 11/2016 | Machida et al. |
| 2017/0216816 A1 | 8/2017 | Matsumoto et al. |
| 2018/0001300 A1 | 1/2018 | Nakatsuru et al. |
| 2018/0185820 A1 | 7/2018 | Tada et al. |
| 2018/0298132 A1 | 10/2018 | Yorino et al. |
| 2020/0122120 A1 | 4/2020 | Tada et al. |

FOREIGN PATENT DOCUMENTS

| | | | |
|---|---|---|---|
| CN | 103930201 A | | 7/2014 |
| CN | 106068297 A | | 11/2016 |
| CN | 107107027 A | | 8/2017 |
| DE | 936263 C | | 12/1955 |
| EP | 0476574 A2 | | 3/1992 |
| JP | 63-118375 | | 5/1988 |
| JP | 64-062317 | | 3/1989 |
| JP | 1992120111 | * | 4/1992 |
| JP | 07-228640 | | 8/1995 |
| JP | H8-89796 | | 4/1996 |
| JP | 2001-79829 A | | 3/2001 |
| JP | 2003-206305 A | | 7/2003 |
| JP | 2004-210924 A | | 7/2004 |
| JP | 2005-29751 A | | 2/2005 |
| JP | 2009-185216 A | | 8/2009 |
| JP | 2009-528412 | | 8/2009 |
| JP | 2009-242466 A | | 10/2009 |
| JP | 2011-213759 A | | 10/2011 |
| JP | 2012-031217 A | | 2/2012 |
| JP | 2012-77157 A | | 4/2012 |
| JP | 2013-034942 A | | 2/2013 |
| JP | 2013-253262 A | | 12/2013 |
| JP | 54-53165 B2 | | 3/2014 |
| WO | 2011/040530 A1 | | 4/2011 |
| WO | WO-2011/126079 A1 | | 10/2011 |
| WO | 2014162843 A1 | | 10/2014 |
| WO | WO-2016/158975 A1 | | 10/2016 |
| WO | WO-2016/204302 A1 | | 12/2016 |

OTHER PUBLICATIONS

International Search Report from corresponding PCT Application No. PCT/JP2021/026205 dated Aug. 31, 2021.

Written Opinion from corresponding PCT Application No. PCT/JP2021/026205 dated Aug. 31, 2021.

Japanese Standards of Pharmaceutical Ingredients, p. 1317-1320 (1989).

Office Action from CN 202180047476.9 dated Jan. 4, 2024.

Extended European Search Report from EP Application No. 21841444.9 dated Oct. 11, 2024.

* cited by examiner

WATER ABSORBING AGENT COMPOSITION AND METHOD FOR PRODUCING SAME

PRIORITY STATEMENT

This application is a national stage application under 35 U.S.C. § 371 of PCT International Application No. PCT/JP2021/026205, which has an international filing date of 13 Jul. 2021 and claims priority under 35 U.S.C. § 119 to Japanese Patent Application No. 2020-120248 filed on 13 Jul. 2020. The contents of each application recited above are incorporated herein by reference in their entirety.

TECHNICAL FIELD

The present invention relates to a water-absorbing agent composition and a method for producing the same.

BACKGROUND ART

Water-absorbing resins (super absorbent polymers (SAPs)) are water-swellable, water-insoluble crosslinked polymers, and are used in various water absorbent articles including hygienic materials (sanitary materials) such as disposable diapers, sanitary napkins, adult incontinence products (incontinence pads), and sheets for pets, agricultural and horticultural water retaining agents for soil, and industrial waterproofing agents.

In recent years, on the basis of viewpoints such as a reduction in the burdens on the global environment, conservation of resources, carbon neutrality, and the sustainable development goals (SDGs) and for the reason that having biodegradability is preferred, moves have been brisk to generally use, instead of exhaustible energy resources including petroleum, so-called sustainable raw materials that are renewable, plant or animal-based organic resources, which are constituents of modern living organisms. Also in the field of water-absorbing resins, research is underway to use, for at least part of a water-absorbing resin, a naturally derived polysaccharide as a sustainable raw material.

For example, Non-Patent Literature 1 indicates that starch grafted sodium polyacrylate obtained through graft polymerization of sodium acrylate and starch is commercially available as a water-absorbing resin. Patent Literatures 1 and 2 disclose methods for producing the water-absorbing resin (starch grafted sodium polyacrylate).

Patent Literature 4 discloses a method for producing a superabsorbent composition (water-absorbing resin composition), the method including adding a starch compound in any step of the production process of a water-absorbing resin.

Further, Patent Literatures 5 and 6 disclose methods for producing a water-absorbing resin, the method including mixing a polysaccharide such as starch into a crosslinked hydrogel polymer obtained after polymerization of a water-absorbing resin. Patent Literatures 7 to 9 also suggest a polyacrylic acid-based water absorbent resin in which cellulose is mixed as a raw material. Patent Literatures 10 to 12 also suggest a polyacrylic acid-based water absorbent resin in which starch is mixed as a raw material. Patent Literature 13 discloses a water-absorbing resin including crosslinked modified starch.

CITATION LIST

Patent Literature

Patent Literature 1

U.S. Pat. No. 4,076,663

Patent Literature 2

Japanese Patent Application Publication, Tokukaishou, No. 54-53165

Patent Literature 3

Japanese Patent Application Publication, Tokukaihei, No. 1-062317

Patent Literature 4

Japanese Translation of PCT International Application, Tokuhyo, No. 2009-528412

Patent Literature 5

EP0476574A2

Patent Literature 6

U.S. Pat. No. 5,340,853

Patent Literature 7

Japanese Patent Application Publication, Tokukai, No. 2009-185216

Patent Literature 8

Japanese Patent Application Publication, Tokukai, No. 2009-242466

Patent Literature 9

Japanese Patent Application Publication, Tokukai, No. 2012-031217

Patent Literature 10

Japanese Patent Application Publication, Tokukai, No. H07-228640

Patent Literature 11

Japanese Patent Application Publication, Tokukai, No. 2013-034942

Patent Literature 12

Japanese Patent Application Publication, Tokukai, No. 2011-213759

Patent Literature 13

Japanese Patent Application Publication, Tokukai, No. 2013-253262

Patent Literature 14

WO2011/126079

Patent Literature 15

WO2016/158975

Patent Literature 16

WO2016/204302

Patent Literature 17

Japanese Patent Application Publication, Tokukai, No. 2001-79829

Patent Literature 18

Japanese Patent Application Publication, Tokukaishou, No. 63-118375

Patent Literature 19

Japanese Patent Application Publication, Tokukai, No. 2004-210924

Patent Literature 20

Japanese Patent Application Publication, Tokukai, No. 2003-206305

Patent Literature 21

Japanese Patent Application Publication, Tokukai, No. 2005-29751

Non-Patent Literature

Non-Patent Literature 1

Japanese standards of pharmaceutical ingredients (1989), pp. 1319 and 1320

SUMMARY OF INVENTION

Technical Problem

Water-absorbing resins, which themselves are originally white, are used mainly in diapers, sanitary napkins, and the like. When used in such products, water-absorbing resins are mixed with white pulp. Accordingly, coloring of the water-absorbing resins are typically unacceptable in terms of hygienic appearance. However, polysaccharides, which is typified by starch used in Patent Literatures 1 to 13, are typically poor in heat resistance. This causes a problem which is that a water-absorbing agent composition obtained through addition of a polysaccharide to a monomer or a water-absorbing resin during production become colored brown or the like by undergoing a step under high temperature conditions during the production (e.g., a step of drying a water-absorbing resin containing water (crosslinked hydrogel polymer) at high temperature or a surface-crosslinking step at high temperature). Further, in consideration of the difficulties in carrying out high-temperature drying treatment and high-temperature surface-crosslinking treatment, when treatment such as drying is carried out at low temperature to reduce the coloring, the inconvenience of decreasing physical properties and productivity of the water-absorbing agent composition is caused. That is to say, a water-absorbing agent composition containing a polysaccharide becomes colored when left under high temperature conditions (under condition of heating at 100° C. or higher) during production thereof. Reducing such coloring requires a restriction on the production process (or production conditions). For an improvement in the physical properties of a water-absorbing resin, surface crosslinking is carried out also after the drying. Nevertheless, such a restriction on the production conditions (drying condition and surface crosslinking condition) typically makes a water-absorbing resin containing a polysaccharide poor in physical properties or expensive.

Accordingly, there are a need for a water-absorbing agent composition of high quality (and stable quality) that can be produced without a decrease in productivity and is not colored even in a production process (or under production conditions) under high temperature conditions (under the condition of heating at 100° C. or higher) even when a polysaccharide is used as a sustainable raw material for at least part of the water-absorbing agent composition, and a need for a method for producing the water-absorbing agent composition.

A main object of an aspect of the present invention is therefore to provide a water-absorbing agent composition of high quality (and stable quality) that can be produced without a decrease in productivity and is not colored due to heating during production, i.e., not colored even in a production process (or under production conditions) under high temperature conditions (under the condition of heating at 100° C. or higher) even when a polysaccharide is used as a sustainable raw material for at least part of the water-absorbing agent composition, and a method for producing the water-absorbing agent composition.

Solution to Problem

The inventors of the present invention conducted various studies to solve the above problems, and eventually found that a reducing agent is effective in preventing a polysaccharide (in particular, starch) mixed with a water-absorbing resin (in particular, crosslinked hydrogel polymer) from becoming colored during heating at high temperature, to bring the present invention to completion. Specifically, the inventors found that the above problems can be solved with a water-absorbing agent composition including a polyacrylic acid (salt)-based water-absorbing resin, a polysaccharide, and a reducing agent, the water-absorbing agent composition being surface-crosslinked, containing the polysaccharide in an amount of 10 mass % or more and containing the reducing agent in an amount of 10 ppm to 10000 ppm, and having a degree of coloration (YI value) of 60 or less, to reach the completion of the present invention.

Specifically, the present invention includes an invention as described in the following <1> to <11>.

<1> A water-absorbing agent composition comprising a polyacrylic acid (salt)-based water-absorbing resin, a polysaccharide, and a reducing agent, the water-absorbing agent composition being surface-crosslinked, the water-absorbing agent composition containing the polysaccharide in an amount of 10 mass % or more and containing the reducing agent in an amount of 10 ppm to 10000 ppm, and the water-absorbing agent composition having a degree of coloration (YI value) of 60 or less.

<2> The water-absorbing agent composition described in <1>, wherein the reducing agent contains one or more compounds selected from the group consisting of an inorganic compound containing a sulfur atom, an organic compound containing a sulfur atom, and an inorganic compound containing a phosphorus atom.

<3> The water-absorbing agent composition described in <1> or <2>, wherein the reducing agent is sodium hydrogen sulfite and/or sodium sulfite.

<4> The water-absorbing agent composition described in any one of <1> to <3>, wherein the polysaccharide is starch and/or a modified starch.

<5> The water-absorbing agent composition described in any one of <1> to <4>, wherein the water-absorbing agent composition contains residual monomers in an amount of 1000 ppm or less.

<6> The water-absorbing agent composition described in any one of <1> to <5>, wherein the water-absorbing agent composition has a fluid retention capacity under pressure (AAP0.3), measured under a pressure of 0.3 kPa, of 10 g/g or more.

<7> A method for producing a water-absorbing agent composition including a polyacrylic acid (salt)-based water-absorbing resin, a polysaccharide, and a reducing agent, the method comprising a polymerization step, a drying step, and a surface-crosslinking step in this order in a production process of the water-absorbing agent composition, at any stage from a time when the polymerization step is started to a time when the surface-crosslinking step is ended, the polysaccharide and the reducing agent being added in an amount of 10 mass % or more and in an amount of 10 ppm to 100000 ppm, respectively, relative to a sum of the mass of a monomer composition introduced in the polymerization step and the mass of the polysaccharide.

<8> The method described in <7>, wherein the polysaccharide is added at or after a time when the polymerization step is ended.

<9> The method described in <7> or <8>, further comprising a gel-crushing step between the polymerization step and the drying step, the polysaccharide being added at at least one time selected from the group consisting of a time before the gel-crushing step is started (and after the polymerization step is ended), a time when the gel-crushing step is started, and a time during the gel-crushing step.

<10> The method described in any one of <7> to <9>, wherein the reducing agent is added in a period from a time when the polymerization step is ended to a time when the drying step is started.

<11> The method described in any one of <7> to <9>, further comprising a gel-crushing step between the polymerization step and the drying step, the reducing agent being added between a time before the gel-crushing step is started (and after the polymerization step is ended) and a time before the surface-crosslinking step is started.

<12> The method described in any one of <7> to <11>, further comprising a gel-crushing step between the polymerization step and the drying step, the reducing agent being added before the gel-crushing step is started (and after the polymerization step is ended) and/or at a time when the gel-crushing step is started.

<13> The method described in <7>, further comprising a gel-crushing step between the polymerization step and the drying step, the polysaccharide being added at at least one time selected from the group consisting of a time before the gel-crushing step is started (and after the polymerization step is ended), a time when the gel-crushing step is started, and a time during the gel-crushing step, and the reducing agent being added between the time before the gel-crushing step is started (and after the polymerization step is ended) and a time before the surface-crosslinking step is started.

<14> The method described in any one of <7> to <13>, wherein the surface-crosslinking step includes a surface-crosslinking reaction at 100° C. to 250° C.

<15> A water-absorbing agent composition produced by the method described in any one of <7> to <14>.

The present invention also includes: <16> the method described in any one of <7> to <14>, further including a gel-crushing step between the polymerization step and the drying step, a crosslinked hydrogel polymer obtained in the polymerization step being crushed such that the crosslinked hydrogel polymer has a mass average particle diameter d1 in terms of the solid content of 1 mm or less; <17> the method described in any one of <7> to <14> and <16> in which the polysaccharide is starch and/or a modified starch; and <18> the method described in <17> in which the starch and/or the modified starch have/has a particle diameter of 1 μm to 1000 μm.

Advantageous Effects of Invention

An aspect of the present invention can advantageously provide a water-absorbing agent composition of high quality (and stable quality) that can be produced without a decrease in productivity and is not colored due to heating during production, i.e., not colored even in a production process (or under production conditions) under high temperature conditions (under the condition of heating at 100° C. or higher) even when a polysaccharide is used as a sustainable raw material for at least part of the water-absorbing agent composition, and a method for producing the water-absorbing agent composition.

DESCRIPTION OF EMBODIMENTS

The following description will discuss embodiments of the present invention in detail. Note that the present invention is not limited to the following embodiments, but can be variously altered within this disclosure. The present invention also encompasses, in its technical scope, any embodiment derived by appropriately combining technical means disclosed in differing embodiments. As used herein, the expression "A to B" representing a numerical range means "A or more and B or less" and the term "ppm" means "ppm by mass" or "ppm by weight", unless otherwise specified. The term "(meth)acrylic" means "acrylic and/or methacrylic". The terms "mass" and "weight" are regarded as being interchangeable with each other. Further, the masses of a water-absorbing resin, a water-absorbing resin composition, a water-absorbing agent composition, and the like represent numerical values in terms of solid content unless otherwise specified.

<1> Definitions of Terms

<1-1> Water-absorbing resin, water-absorbing resin composition, water-absorbing agent composition As used herein, a water-absorbing resin means a water-swellable, water-insoluble crosslinked polymer, and is typically in the form of a particle. Being water-swellable means that the fluid retention capacity without pressure (CRC) defined in NWSP 241.0.R2 (15) is 5 g/g or more. Being water-insoluble means that the soluble component (Ext) defined in NWSP 270.0.R2 (15) is contained in an amount of 50 mass % or less.

The water-absorbing resin is a hydrophilic crosslinked polymer obtained by crosslinking and polymerizing unsaturated monomers each having a carboxyl group.

As used herein, the water-absorbing resin can refer to a "polymer that is only internally crosslinked, i.e., a polymer having an internal crosslink density and a surface crosslink density that are substantially the same" or a "polymer that is both internally crosslinked and surface-crosslinked, i.e., a polymer having an internal crosslink density and a surface crosslink density that is higher than the internal crosslink density".

As used herein, in principle, the "polymer that is only internally crosslinked" and the "polymer that is both internally crosslinked and surface-crosslinked" are both referred to as a "water-absorbing resin" without being distinguished from each other. However, when it is necessary to clearly distinguish between the presence and the absence of a surface crosslink, the "polymer that is only internally crosslinked" is referred to as a "water-absorbing resin before surface crosslinking" or a "base polymer" because such a polymer is before being subjected to surface crosslinking, and the "polymer that is both internally crosslinked and surface-crosslinked, i.e., the polymer having an internal crosslink density and a surface crosslink density that is higher than the internal crosslink density" is referred to as a "water-absorbing resin after surface crosslinking" or a "water-absorbing resin having been surface-crosslinked" because such a polymer is after being subjected to surface crosslinking. Note that the phrase "before surface crosslinking" means "before a surface-crosslinking agent is added" or "before a surface-crosslinking reaction by heating treatment starts even after a surface-crosslinking agent is added".

As used herein, the term "water-absorbing resin" refers only to a resin component. When a component other than a resin such as an additive is included, a term "water-absorbing resin composition" is used as a representation. Further, when the water-absorbing resin not having been surface-crosslinked contains an additive or any other component, a term "water-absorbing resin composition before surface crosslinking" or a "base polymer composition" is used as a representation. When the water-absorbing resin having been surface-crosslinked contains an additive or any other component, a term "water-absorbing resin composition after surface crosslinking" or a "water-absorbing resin composition having been surface-crosslinked" is used as a representation.

As used herein, a "water-absorbing resin composition" at a stage of being shipped as an end product is referred to particularly as a "water-absorbing agent composition".

<1-2> Acrylic acid (salt)-based monomer composition, polyacrylic acid (salt)-based water-absorbing resin As used herein, the term "acrylic acid (salt)" means acrylic acid and/or a salt thereof. The term "acrylic acid (salt)-based monomer composition" means a monomer composition containing the acrylic acid (salt) in an amount of 50 mol % or more relative to the total amount of monomers except an internal crosslinking agent.

As used herein, a polyacrylic acid (salt)-based water-absorbing resin means a crosslinked polymer obtained by using the above acrylic acid (salt)-based monomer composition as raw material. In other words, the polyacrylic acid (salt)-based water-absorbing resin is a crosslinked polymer that contains acrylic acid (salt)-derived structural units in an amount of 50 mol % or more relative to the total amount of structural units constituting the polyacrylic acid (salt)-based water-absorbing resin and that contains a graft component, which is an optional component.

Specifically, the polyacrylic acid (salt)-based water-absorbing resin is a polymer obtained by using the acrylic acid (salt) as a raw material in an amount which is preferably 50 mol % or more, more preferably 70 mol % or more, and even more preferably 90 mol % or more and which is preferably 100 mol % or less and particularly preferably substantially 100 mol %, relative to all of a monomer component involved in a polymerization reaction except an internal crosslinking agent.

A water-absorbing resin composition or a water-absorbing agent composition in which a polyacrylic acid (salt)-based water-absorbing resin is a main component means a composition containing a polyacrylic acid (salt)-based water-absorbing resin in an amount of 50 mass % or more.

<1-3> NWSP

NWSP, which is the acronym for Non-Woven Standard Procedures-Edition 2015, was issued jointly by the European Disposables and Nonwovens Associations (EDANA) and the Association of the Nonwoven Fabrics Industry (INDA) and describes a unified method in Europe and the United States for evaluating a nonwoven fabric and a product of the same. NWSP also describes a standard method for measuring a water-absorbing resin. In the present specification, the physical properties of a water-absorbing resin (water-absorbing resin composition or water-absorbing agent composition) are measured in conformity with the original of NWSP (2015).

In the present specification, a method for measuring the various physical properties of a water-absorbing resin, a water-absorbing resin composition, or a water-absorbing agent composition is in conformity with the measurement methods in Examples below, unless otherwise stated.

<2> Water-Absorbing Agent Composition

A water-absorbing agent composition in accordance with an embodiment of the present invention is a water-absorbing agent composition including a polyacrylic acid (salt)-based water-absorbing resin, a polysaccharide, and a reducing agent, the water-absorbing agent composition being surface-crosslinked, containing the polysaccharide in an amount of 10 mass % or more and containing the reducing agent in an amount of 10 ppm to 10000 ppm, and having a degree of coloration (YI value) of 60 or less.

In the water-absorbing agent composition, surface crosslinking is performed with the polyacrylic acid (salt)-based water-absorbing resin and the polysaccharide being in the form of being mixed together and/or kneaded (with the water-absorbing resin and the polysaccharide being in the state of being mixed together to be united together). It is preferable to perform surface crosslinking with the water-absorbing resin and the polysaccharide being in the state of being mixed together to be united together. The form is, for example, a form in which surface-crosslinked is, for example, a composite resin including a polyacrylic acid (salt)-based water-absorbing resin and a polysaccharide kneaded and mixed into the polyacrylic acid (salt)-based water-absorbing resin, or a polyacrylic acid (salt)-polysaccharide complex obtained through polymerization which is performed in the presence of a polysaccharide and in which used as raw materials are an acrylic acid (salt)-based monomer and an internal crosslinking agent. The water-absorbing agent composition may include a polyacrylic acid (salt)-based water-absorbing resin and/or a polysaccharide that is/are present solely, and the polysaccharide that is exposed at the surface of the composite resin may have a portion that has not been surface-crosslinked.

[Polyacrylic Acid (Salt)-Based Water-Absorbing Resin]

The polyacrylic acid (salt)-based water-absorbing resin (hereinafter referred to simply as "water-absorbing resin") is a crosslinked polymer obtained by polymerizing, in the presence of a polymerization initiator, monomer compositions whose main component is an acrylic acid (salt)-based monomer.

(a) Monomer

The monomer is a raw material component (monomer) for forming a water-absorbing resin (polymer). The monomer includes an acrylic acid (salt)-based monomer, a monomer other than an acrylic acid (salt)-based monomer, and an internal crosslinking agent. All monomers forming the water-absorbing resin correspond to a monomer composition. Examples of the acrylic acid (salt)-based monomer include (meth)acrylic acid and a salt thereof.

Among monomers (ethylenic unsaturated monomers) having an unsaturated double bond, a monomer containing an acid group is preferable as a monomer that is other than an acrylic acid (salt)-based monomer and that may be included in the monomer composition. Specific examples of such a monomer include maleic acid (anhydride), fumaric acid, crotonic acid, itaconic acid, 2-(meth) acryloyl ethane-sulfonic acid, 2-(meth) acryloyl propanesulfonic acid, 2-(meth)acrylamide-2-methylpropane sulfonic acid, vinylsulfonic acid, styrene sulfonic acid, and salts thereof. One monomer or two or more monomers of these monomers is/are used as appropriate.

Examples of the salts described above include alkali metal salts, ammonium salts, and amine salts. The salts are preferably a sodium salt, a potassium salt, a lithium salt, and an ammonium salt, and particularly preferably a sodium salt.

The monomer composition whose main component is the acrylic acid (salt)-based monomer is neutralized preferably in a range of 10 mol % to 90 mol %, more preferably 40 mol % to 80 mol %, and particularly preferably 60 mol % to 75 mol %.

Therefore, the monomer composition whose main component is the acrylic acid (salt)-based monomer is neutralized preferably with a neutralizing solution containing an alkali metal hydroxide such as sodium hydroxide, potassium hydroxide, or lithium hydroxide, a (hydrogen) carbonate such as sodium (hydrogen) carbonate or potassium (hydrogen) carbonate, or a monovalent basic compound such as ammonia, and particularly preferably with a neutralizing solution containing sodium hydroxide.

The monomer composition may be neutralized after being polymerized. In other words, the crosslinked hydrogel polymer (hereinafter referred to as "hydrogel") may be neutralized to be a neutralized product. However, in consideration of, for example, the productivity of the water-absorbing resin, and various physical properties, it is more preferable to use a neutralized monomer composition for polymerization to obtain a hydrogel.

The monomer composition may contain, as appropriate, a hydrophilic or hydrophobic unsaturated monomer (hereinafter referred to as "any other monomer") in addition to the above-described monomer. Examples of the any other monomer include N-vinyl-2-pyrrolidone, N-vinyl acetamide, (meth)acrylamide, N-isopropyl (meth)acrylamide, N,N-dimethyl (meth)acrylamide, 2-hydroxyethyl (meth) acrylate, methoxy polyethylene glycol (meth)acrylate, polyethylene glycol (meth)acrylate, and stearyl acrylate. The amount of the any other monomer used only needs to be enough to prevent impairment of the physical properties of a resultant water-absorbing agent composition. Specifically, the amount used is 50 mol % or less and more preferably 20 mol % or less, relative to the amount of the monomer composition except the internal crosslinking agent.

(b) Internal Crosslinking Agent

Examples of the internal crosslinking agent include: a compound having at least two polymerizable double bonds in the molecule of the compound, such as N,N'-methylenebisacrylamide, (poly)ethylene glycol di(meth)acrylate, (poly)propylene glycol di(meth)acrylate, (polyoxyethylene) trimethylolpropane tri(meth)acrylate, trimethylolpropane di(meth)acrylate, polyethylene glycol di(β-acryloyloxypropionate), trimethylolpropane tri(β-acryloyloxypropionate), and poly(meth)allyloxyalkane; and a compound capable of forming a covalent bond by reaction with a carboxyl group, such as a polyglycidyl ether (e.g., ethylene glycol diglycidyl ether) and a polyol (e.g., ethylene glycol, polyethylene glycol, glycerin, sorbitol). The internal crosslinking agent is more preferably the compound having at least two polymerizable double bonds in the molecule of the compound. One internal crosslinking agent or two or more internal crosslinking agents of these internal crosslinking agents is/are used as appropriate.

In consideration of the physical properties of a resultant water-absorbing agent composition, the internal crosslinking agent is used in a range of preferably 5.0 mol % or less, more preferably 2.0 mol % or less, even more preferably 0.5 mol % or less, particularly preferably 0.1 mol % or less, and most preferably 0.01 mol % to 0.1 mol %, relative to the amount of all monomers that correspond to the monomer composition except the internal crosslinking agent. Further, a crosslinking method in which the internal crosslinking agent is used can be used in combination with radical self-crosslinking during polymerization, radiation crosslinking, or any other publicly known crosslinking method.

(c) Polymerization Initiator

Examples of the polymerization initiator include a photolytic-type polymerization initiator, a pyrolysis-type polymerization initiator, and a redox-type polymerization initiator. The amount of the polymerization initiator used is in a range of preferably 0.0001 mol % to 1 mol % and more preferably 0.0005 mol % to 0.5 mol %, relative to the amount of all monomers that correspond to the monomer composition except the internal crosslinking agent. Examples of the photolytic-type polymerization initiator include a benzoin derivative, a benzyl derivative, an acetophenone derivative, a benzophenone derivative, and an azo compound. Examples of the pyrolysis-type polymerization initiator include a persulfate (sodium persulfate, potassium persulfate, ammonium persulfate), a peroxide (hydrogen peroxide, t-butyl peroxide, methyl ethyl ketone peroxide), and an azo compound (e.g., 2,2'-azobis(2-amidinopropane) dihydrochloride, 2,2'-azobis [2-(2-imidazoline-2-yl)propane]dihydrochloride). Examples of the redox-type polymerization initiator include an initiator in which the persulfate or the peroxide (oxidizing agent) is combined with a reducing compound (reducing agent) such as L-ascorbic acid or sodium hydrogen sulfite. In a case of using the redox-type polymerization initiator, use in combination with a persulfate is more preferable because it is possible to reduce the amount of unreacted monomers (residual monomers) contained in a water-absorbing agent composition, which becomes an end product after undergoing a polymerization step.

It is also preferable to use the photolytic-type polymerization initiator and the pyrolysis-type polymerization initiator in combination. In this case, the combination use ratio (molar ratio), which may be set as appropriate, is preferably 1/100 to 100/1 and more preferably 1/10 to 10/1.

Note that the persulfate and the peroxide used as the polymerization initiators are consumed during the polymerization of the monomer composition and do not remain in a resultant water-absorbing agent composition.

Alternatively, the polymerization can be carried out by using active energy rays such as ultraviolet rays in combination with or not in combination with the polymerization initiator.

(d) Solvent

A solvent to be used during the polymerization of the monomer composition is not limited to any particular solvent. In other words, a publicly known solvent can be used as appropriate for the polymerization of the monomer composition. As the publicly known solvent, deionized water (ion-exchange water) is preferable. A monomer composition obtained with use of the deionized water (ion-exchange water) is particularly referred to as an aqueous monomer solution.

[Polysaccharide]

Examples of a polysaccharide that can be used in the present invention include natural polysaccharides derived from the inside of living organisms and modified products of such polysaccharides. These polysaccharides, in which any fossil material such as petroleum is not used, are deemed to be renewable raw materials. The polysaccharides are polymers having a backbone containing a monosaccharide repeating unit. Examples of the polysaccharide include starch, amylopectin, amylose, cellulose, galactomannan, glucomannan, xanthan gum, carrageenan, chitin, chitosan, and modified products thereof. Examples of the starch include cornstarch, potato starch, wheat starch, tapioca starch, waxy cone starch, rice starch, and sweet potato starch. Examples of the cellulose include a pulp derived from cotton or wood, bacterial cellulose, lignocellulose, regenerated cellulose (e.g., cellophane, regenerated fiber), and microcrystalline cellulose. Examples of the galactomannan include guar gum, locust bean gum, tara gum, and cassia gum.

Examples of a modification method for obtaining modified starch, modified amylopectin, modified amylose, modified cellulose, modified galactomannan, modified glucomannan, modified xanthan gum, modified carrageenan, and the like include esterification such as acetylation treatment, etherification such as carboxy-alkylation, phosphorylation, oxidation, sulfation, phosphoric acid crosslinking, adipic acid crosslinking, enzyme treatment, and a combination thereof. The number of types of substituents introduced by the modification may be one, or may be two or more. The degree of substitution in a case of the modified products is preferably 2 or less, more preferably 1 or less, even more preferably 0.5 or less, and particularly preferably 0.25 or less, in consideration of the physical properties of a resultant water-absorbing agent composition.

The polysaccharide may be crosslinked. The polysaccharide can be crosslinked by any publicly known method. Specifically, the polysaccharide may be crosslinked with use of a crosslinking agent, or may be crosslinked with use of radiation (e.g., radiation such as a gamma ray, an x-ray, an electron beam) and/or heat. Examples of the crosslinking agent include an N-methylol compound (e.g., dimethylol ethylene urea, dimethylol dihydroxy ethylene urea) having a ring portion in the molecule thereof, a polycarboxylic acid (e.g., citric acid, tricarballylic acid, butanetetracarboxylic acid), a multifunctional epoxy compound (e.g., ethyleneglycol diglycidyl ether, propylene glycol diglycidyl ether, glycerol diglycidyl ether), a polyvalent metal ion (e.g., aluminum ion, chromium ion), a multifunctional amine (e.g., amino acid, polyamine, triamine, diamine), and multifunctional aldehydes (e.g., glutaraldehyde, glyoxal). One crosslinking agent or two or more crosslinking agents of these crosslinking agents may be used as appropriate.

Among the polysaccharides above, starch, cellulose, and modified products thereof are more preferable, unmodified starch and unmodified cellulose are even more preferable, and unmodified starch is most preferable, in terms of easy availability and the like. In particular, starch is capable of being given fluidity by gelatinization (alpha-modification), and is therefore capable of being uniformly mixed into a water-absorbing resin by kneading. It is therefore possible to reduce segregation of the polysaccharide (presence of the polysaccharide alone in a greater amount) in the water-absorbing resin composition. Accordingly, starch is most preferable.

One polysaccharide or two or more polysaccharides of these polysaccharides is/are used as appropriate. The polysaccharide has a particle diameter in a range of preferably 1 μm to 1000 μm, more preferably 1 μm to 500 μm, and even more preferably 1 μm to 200 μm. When the polysaccharide is starch, the particle diameter thereof is in a range of preferably 1 μm to 150 μm and more preferably 1 μm to 100 μm.

The polysaccharide has a molecular weight of preferably 500 or more, more preferably 1000 or more, even more preferably 2000 or more, particularly preferably 5000 or more, and most preferably 10000 or more. The molecular weight of the polysaccharide has an upper limit that is not limited to any particular value, but the upper limit is preferably 10,000,000 or less, more preferably 8,000,000 or less, and even more preferably 5,000,000 or less. When the molecular weight of the polysaccharide is less than 500, the water-absorbing agent composition could have a decreased fluid retention capacity. When the molecular weight of the polysaccharide exceeds 10,000,000, the handleability of the polysaccharide becomes poor.

The polysaccharide is contained in the water-absorbing agent composition in an amount of preferably 10 mass % or more and more preferably 20 mass % or more, with the total amount of the water-absorbing agent composition being 100 mass %. The polysaccharide content has an upper limit of preferably 50 mass % or less and more preferably 30 mass % or less. Therefore, as described later, the polysaccharide is added to the water-absorbing resin, preferably to a hydrogel, such that the polysaccharide content of a resultant water-absorbing agent composition falls within the above described amounts. When the polysaccharide content is less than 10 mass %, the polysaccharide as a sustainable raw material is used in a reduced amount. When the polysaccharide content exceeds 50 mass %, the water-absorbing agent composition could have a decreased fluid retention capacity.

[Reducing Agent]

The reducing agent contains one or more compounds selected from the group consisting of an inorganic compound containing a sulfur atom, an organic compound containing a sulfur atom, and an inorganic compound containing a phosphorus atom. Examples of the inorganic compound containing a sulfur atom include: a sulfite (e.g., sodium sulfite, potassium sulfite, ammonium sulfite); a hydrogen sulfite (e.g., sodium hydrogen sulfite, potassium hydrogen sulfite, ammonium hydrogen sulfite); a ferrous salt (e.g., ferrous sulfate); and a cuprous salt (e.g., cuprous sulfate). Examples of the organic compound containing a sulfur atom include 2-hydroxy-2-sulfonato acetic acid and a salt thereof; and 2-hydroxy-2-sulfinato acetic acid and a salt thereof. Examples of the inorganic compound containing a phosphorus atom include: phosphorous acid and a phosphite (e.g., disodium phosphite, dipotassium phosphite, diammonium phosphite), a hydrogen phosphite (e.g., sodium hydrogen phosphite, potassium hydrogen phosphite, ammonium hydrogen phosphite); and hypophosphorous acid and a hypophosphite (e.g., sodium hypophosphite, potassium hypophosphite, ammonium hypophosphite). One reducing agent or two or more reducing agents of these reducing agents is/are used as appropriate. Among the above reducing agents, a reducing agent containing the inorganic compound containing a sulfur atom is preferable, and sodium hydrogen sulfite and sodium sulfite are more preferable.

The reducing agent content of the water-absorbing agent composition is in a range of preferably 10 ppm to 10000 ppm, more preferably 30 ppm to 5000 ppm, and even more preferably 50 ppm to 3000 ppm, relative to the total amount of the water-absorbing agent composition. Therefore, as described later, the reducing agent is added to the water-absorbing resin, preferably to a hydrogel, such that the reducing agent content of a resultant water-absorbing agent composition falls within the above described amounts. When the reducing agent content falls below the above ranges, the water-absorbing agent composition becomes colored due to heating during the production. When the reducing agent content exceeds the above ranges, various physical properties (water absorption physical properties) of the water-absorbing agent composition deteriorate.

[Optional Component]

The water-absorbing agent composition can contain a water-soluble resin or a water-absorbing resin such as polyvinyl alcohol or polyethylene imine; a thermoplastic resin such as polyethylene or polypropylene; a blowing agent (e.g., a carbonate, an azo compound, a gas bubble); a surfactant; an additive (a deodorant, an antibacterial agent, a perfume; inorganic powder such as silicon dioxide or titanium oxide; a pigment, a dye, a hydrophilic short fiber, a plasticizer); a chelating agent such as trisodium diethylenetriamine pentaacetate (DTPA-3Na); and hydroxycarboxylic acid, which are optional components. When the optional component is the water-soluble resin, the water-absorbing resin, or the thermoplastic resin, the amount of the optional component added is preferably 50 mass % or less, more preferably 20 mass % or less, particularly preferably 10 mass % or less, and most preferably 3 mass % or less, relative to the amount of all monomers that correspond to the monomer composition except the internal crosslinking agent. When the optional component is the blowing agent, the surfactant, or the additive, the amount of the optional component added is preferably 5 mass % or less and more preferably 1 mass % or less. When the optional component is the chelating agent or the hydroxycarboxylic acid, the amount of the optional component added is in a range of preferably 10 ppm to 5000 ppm, more preferably 10 ppm to 1000 ppm, even more preferably 50 ppm to 1000 ppm, and particularly preferably 100 ppm to 1000 ppm.

With the water-absorbing agent composition in accordance with an embodiment of the present invention, it is possible to reduce "coloration caused by heating during the production" observed in conventional water-absorbing agent compositions containing a polysaccharide. Just for the record, such a reduction in "coloration caused by heating during the production" greatly differs in mechanism from the object of Patent Literatures 7 to 9 that is "prevention of coloration, with lapse of time, of a water-absorbing resin composition that does not contain a polysaccharide". Specifically, the "coloration caused by heating during the production" observed in a water-absorbing agent composition that contains a polysaccharide is caused by, for example, subjecting a base polymer composition that contains a polysaccharide (starch) and a polyacrylic acid (salt)-based water-absorbing resin to a step such as a surface-crosslinking step at 150° C. or higher (i.e., coloration immediately after a production process), whereas the "coloration with lapse of time" observed in a water-absorbing agent composition that does not contain a polysaccharide is coloration caused, for example, in a week under conditions of 90° C. and 90% RH (i.e., caused during a storage period that follows the production). Both of these kinds of coloration therefore differ from each other.

<3> Method for Producing Water-Absorbing Agent Composition

A method, in accordance with an embodiment of the present invention, for producing the water-absorbing agent composition is a method for producing a water-absorbing agent composition containing a polyacrylic acid (salt)-based water-absorbing resin, a polysaccharide, and a reducing agent, the method including a polymerization step, a drying step, and a surface-crosslinking step in this order in a production process of the water-absorbing agent composition, the polysaccharide and the reducing agent being added in an amount of 10 mass % or more and in an amount of 10 ppm to 100000 ppm, respectively, relative to a sum of the mass of a monomer composition introduced in the polymerization step and the mass of the polysaccharide, at any stage from a time when the polymerization step is started to a time when the surface-crosslinking step is ended.

[Polymerization Step]

A method for polymerizing the monomer composition is not limited to any particular method, but a publicly known reversed phase suspension polymerization method or aqueous solution polymerization method can be used. The reversed phase suspension polymerization method is a polymerization method of causing an aqueous solution of a monomer composition (hereinafter referred to as "aqueous monomer solution") in a hydrophobic organic solvent (dispersion medium) for polymerization. The aqueous solution polymerization method is a polymerization method of polymerizing an aqueous monomer solution with no use of a dispersion solvent. Among the above polymerization methods, the aqueous solution polymerization method is preferable in view of, for example, productivity, ease of control of polymerization, and various physical properties of a resultant water-absorbing resin. With these polymerizations, a crosslinked polymer containing water (hydrogel) is obtained.

Examples of the aqueous solution polymerization method include a static polymerization method of polymerizing an aqueous monomer solution in a static condition and a stir polymerization method of polymerizing an aqueous monomer solution in a stirring device.

The static polymerization method is more preferably a continuous static polymerization method in which an endless belt or a polymerization vessel is used. The endless belt is preferably a belt made of a resin or rubber that is less prone to dissipate polymerization heat from the surface on which a material touches. The polymerization vessel preferably has an open space present in an upper part thereof.

In a case of using the endless belt, the aqueous monomer solution is typically supplied in such an amount that the depth of the aqueous monomer solution on the endless belt is in a range of preferably 1 mm to 100 mm, more preferably 3 mm to 50 mm, and even more preferably 5 mm to 30 mm. When the depth of the aqueous solution is less than 1 mm, temperature control of the aqueous monomer solution could become difficult. When the depth of the aqueous monomer solution exceeds 100 mm, removal of polymerization heat could become difficult.

In the stir polymerization method, a stirrer with a single shaft or a stirrer with two or more shafts is suitably used. The stir polymerization method is preferably a continuous kneader polymerization or the like.

In an embodiment of the present invention, the concentration of an active component (a sum of the monomer composition, the polymerization initiator, and the optional component) in the aqueous monomer solution is not limited to any particular value, but is in a range of preferably 30 mass % to 80 mass %, more preferably 40 mass % to 70 mass %, and even more preferably 45 mass % to 65 mass %. When the concentration of the active component is less than 30 mass %, the productivity of the water-absorbing agent composition can decrease. When the concentration of the active component exceeds 70 mass %, the fluid retention capacity of the water-absorbing agent composition can decrease.

The neutralization of monomers during the preparation of the aqueous monomer solution is preferably carried out in a state of heat insulation. Further, it is more preferable to continuously carry out the neutralization of the monomers while continuously carrying out polymerization. This makes it possible to effectively use heat generated due to neutralization and/or hydration to raise the temperature of the aqueous monomer solution.

It is also possible to suitably use the heat generated due to neutralization and/or hydration to remove oxygen dissolved and remaining in the aqueous monomer solution. Using the heat of neutralization and/or hydration eliminates the need to blow an inert gas into the aqueous monomer solution or degas through decompression to volatilize and thereby remove the dissolved and remaining oxygen that inhibits polymerization. Specifically, the temperature of the aqueous monomer solution is raised with use of the heat of neutralization and/or hydration so that the oxygen dissolved and remaining in the aqueous monomer solution is reduced to preferably 4 mg/L or less, more preferably 2 mg/L or less, and even more preferably 1 mg/L or less. It is preferable to stir, in an atmosphere of an inert gas (preferably nitrogen), the prepared aqueous monomer solution gently enough to avoid taking in a gas bubble.

It is also preferable to remove oxygen from some or all of the monomer composition, the neutralizing solution, the deionized water (ion-exchange water), and any other component before the aqueous monomer solution is prepared, and further remove dissolved and remaining oxygen with use of the heat of neutralization and/or hydration when the aqueous monomer solution is prepared. However, in a case of line-mixing the monomer composition and the neutralizing solution while line-mixing the polymerization initiator to start polymerization at 80° C. or more, it is preferable to reduce the amount of oxygen to be removed from the monomer composition, the neutralizing solution, the deionized water (ion-exchange water), and any other component or even not to remove the oxygen, in order to prevent polymerization from being started during the line-mixing.

Although the polymerization is carried out typically under atmospheric pressure in view of, for example, easy operability, it is also preferable to carry out polymerization while distilling water under reduced pressure to lower the boiling temperature of the aqueous monomer solution.

A polymerization start temperature is not limited to any particular temperature, but is typically in a range of preferably 20° C. to 105° C., more preferably 50° C. to 100° C., even more preferably 60° C. to 100° C., and most preferably 70° C. to 100° C. When the polymerization start temperature is less than 20° C., a polymerization time increases. This can cause a reduction in the productivity of the water-absorbing agent composition and/or deterioration of various physical properties of the water-absorbing agent composition. When the polymerization start temperature exceeds 105° C., the productivity is improved, but an induction time (a period from the point in time when conditions for starting the polymerization are met to the time when the polymerization is actually started) decreases. This can make it difficult to control the polymerization when an operation of mixing the polymerization initiator and any other operation are carried out. In order for the polymerization start temperature to be increased to 50° C. or more, the polymerization device and/or the aqueous monomer solution may be heated. However, it is preferable to use the above-described heat of neutralization and/or hydration.

The polymerization start temperature can be measured through observation of, for example, cloudiness of the aqueous monomer solution, a rise in viscosity, and a rise in temperature. In a case of using active energy rays such as ultraviolet rays, a redox-type polymerization initiator, and an azo compound to carry out the polymerization, the induction time is typically as short as approximately 1 seconds to 1 minutes. The polymerization start temperature may therefore be defined with a temperature which the aqueous monomer solution has immediately before the addition of the polymerization initiator or the irradiation with the active energy rays.

The maximum temperature reached (peak temperature) during the polymerization is not limited to any particular temperature, but is in a range of preferably 60° C. to 150° C., more preferably 70° C. to 140° C., even more preferably 80° C. to 130° C., particularly preferably 85° C. to 120° C., and most preferably 90° C. to 115° C. When the maximum temperature reached exceeds 150° C., various physical properties of a resultant water-absorbing agent composition can deteriorate. The maximum temperature reached refers to a temperature which is measured at the point in time when a temperature rise stops (the point in time when a temperature change ceases) in the measurement of polymerization solution temperature that is carried out every other minute after the polymerization is started.

The polymerization time is not limited to any particular length of time, but is in a range of preferably 1 second to 60 minutes, more preferably 10 seconds to 40 minutes, even more preferably 15 seconds to 10 minutes, and most preferably 30 seconds to 3 minutes. When the polymerization time exceeds 60 minutes, the productivity of a resultant water-absorbing agent composition can decrease and/or various physical properties of the resultant water-absorbing agent composition can deteriorate. The polymerization time refers to a period from the point in time when the conditions for starting the polymerization are met (the time when irradiation with light is started in a case of using a photolytic-type polymerization initiator, or the point in time when the polymerization initiator is added to the aqueous monomer solution in a case of using a pyrolysis-type polymerization initiator or the like) to the time when the maximum temperature reached is achieved. That is, "polymerization time=(induction time)+(time from when polymerization is actually started to when the maximum temperature reached is achieved)".

Therefore, the time when the polymerization step is started refers to a point in time when the conditions for starting the polymerization are met. The time when the polymerization step is ended refers to a point in time when the maximum temperature reached is achieved. At the point in time when the polymerization is ended, a hydrogel is obtained. A hydrogel to be used is not limited to the hydrogel obtained at the point in time when the polymerization is ended, but may be the hydrogel obtained in the stage prior to the end of the polymerization (a stage during the polymerization) only to the extent that the effect of the present embodiment is not undermined.

A solid content increase rate during the polymerization is preferably 1 mass % or more, more preferably 2 mass % or more, and even more preferably 3 mass % or more. Note that the solid content increase rate is defined as the difference between the solid content of the aqueous monomer solution and the solid content of the obtained hydrogel.

The solid content of the hydrogel obtained in the polymerization step is at a concentration falling within a range of preferably 40 mass % to 70 mass % and more preferably 45 mass % to 55 mass %.

[Gel-Crushing Step]

The hydrogel obtained in the polymerization step may be supplied, as it is, for used in the drying step. However, in a case where the hydrogel is obtained by, for example, an aqueous solution polymerization method, it is preferable to crush (cut into small pieces) the hydrogel with use of a crusher such as a gel-crusher so that the size of the crushed hydrogel is reduced to approximately one-tenth or less, and supply the crushed gel for use in the drying step. Further, when the hydrogel is crushed, a small amount of water or water vapor may be added as appropriate.

In the gel-crushing step, the hydrogel obtained in the polymerization step is crushed such that the hydrogel has a mass average particle diameter d1 of 1 mm or less, more preferably 800 μm or less, and even more preferably 500 μm or less, in terms of the solid content. This leads to uniform mixing and kneading of the water-absorbing resin, the polysaccharide, and the reducing agent, and thereby makes it possible to evenly exert the coloration reduction effect throughout the water-absorbing agent composition.

Gel-crushing is carried out by various methods. Specific examples of the gel-crushing method include a method of crushing a gel by using a screw extruder (meat chopper) that includes a die having multiple holes of arbitrary shapes to exclude the gel from the extruder. The gel-crushing may be carried out with the use of a plurality of devices in combination. Examples of a suitably usable gel-crushing method include the methods disclosed in Patent Literatures 14 to 17 (WO2011/126079, WO2016/158975, WO2016/204302, and Japanese Patent Application Publication, Tokukai, No. 2001-79829).

Accordingly, a time when the gel-crushing step is started refers to a point in time when the hydrogel is fed into the crusher such as a gel-crusher, and a time before the gel-crushing step is started (and after the polymerization step is ended) refers to a period from the time when the polymerization step is ended to the time when the gel-crushing step is started. Further, time during the gel-crushing step refers to a period after the time when the gel-crushing step is started and before the gel is discharged from the crusher as a crushed substance.

The solid content of the hydrogel having been crushed (hereinafter referred to as a particulate hydrogel) has a concentration of preferably 50 mass % to 80 mass %, and more preferably 55 mass % to 70 mass %.

[Drying Step]

Drying a particulate hydrogel having been crushed provides a dried material. Examples of a method for the drying include various methods such as heat drying, hot air drying, drying under reduced pressure, infrared drying, microwave drying, drum dryer drying, band drying, drying by azeotropic dehydration with a hydrophobic organic solvent, and high humidity drying with use of high temperature water vapor. Among these, hot air drying with use of a gas whose dew point is 40° C. to 100° C. (more preferably 50° C. to 90° C.) is more preferable.

A drying temperature is not limited to any particular temperature, but in a range of preferably 100° C. to 200° C., more preferably 120° C. to 180° C., and even more preferably 140° C. to 160° C. In a case of hot air drying, the temperature of the hot air is in a range of preferably 100° C. to 200° C., more preferably 120° C. to 180° C., and even more preferably 140° C. to 160° C.

A drying time may be set as appropriate, and not limited to any particular time. The drying time is in a range of preferably approximately 10 seconds to 2 hours, more preferably approximately 1 minute to 1.5 hours, and even more preferably approximately 10 minutes to 1 hour.

Immediately before being fed into the dryer, the particulate hydrogel has a surface temperature which is in a range of preferably 40° C. to 110° C., and more preferably 60° C. to 100° C. When the surface temperature is less than 40° C., a balloon-shaped, dried material is formed during the drying and a large amount of fine powder is therefore generated during pulverization. This can cause deterioration of various physical properties of the water-absorbing agent composition.

A period of time until the particulate hydrogel having been subjected to the gel-crushing step is fed into the dryer is preferably short so that a resultant water-absorbing agent composition is prevented from becoming colored. This period of time is preferably 2 hours or less, more preferably 1 hour or less, even more preferably 30 minutes or less, particularly preferably 10 minutes or less, and most preferably 2 minutes or less.

Accordingly, a time when the drying step is started refers to a point in time when the particulate hydrogel is fed into the dryer.

In the drying step, the moisture content of the obtained dried material is in a range of preferably 3 mass % to 15 mass %, more preferably 4 mass % to 14 mass %, even more preferably 5 mass % to 13 mass %, and particularly preferably 6 mass % to 12 mass %. When the moisture content of the dried material falls below 3 mass %, various physical properties of the water-absorbing agent composition can deteriorate. When the moisture content of the dried material exceeds 15 mass %, crushing the dried material in the pulverizing step can become difficult.

[Pulverizing Step]

The dried material (water-absorbing resin or water-absorbing resin composition; hereinafter, referred to as water-absorbing resin or the like) obtained in the drying step may be pulverized as appropriate so that particles having a size falling within a predetermined range are obtained. The pulverization method is not limited to any particular method. Examples of the method include a method with use of, for example, a vibration mill, a roll granulator, a knuckle-type pulverizer, a roll mill, a high-speed rotary pulverizer (a pin mill, a hammer mill, a screw mill, a roll mill), and a cylindrical mixer.

The water-absorbing resin or the like after the pulverization (pulverized substance) can assume any shape, and is, for example, a granular, powdery, flaky, or fibrous.

[Classification Step]

The pulverized substance (water-absorbing resin or the like) obtained in the pulverizing step may be classified as appropriate so that particles (classified substances) having sizes falling within a predetermined range are separated. The classification is not limited to any particular method. Examples of the method include separation with use of a sieve. Specifically, for example, in a case of obtaining water-absorbing resins or the like (classified substances) having sizes of 150 μm to 850 μm, classification may be carried out as follows: first separate the pulverized substances with use of a 850-μm mesh sieve; then separate the pulverized substances having passed through the 850-μm mesh sieve with use of a 150-μm mesh sieve; and then collect the pulverized substances that have not passed through (that remain on) the 150-μm mesh sieve.

The mass average particle diameter (D50) of the water-absorbing resins or the like (classified substances) before surface crosslinking is not limited to any particular value, but is in a range of preferably 250 μm to 450 μm, more preferably 275 μm to 425 μm, and even more preferably 300 μm to 400 μm. Containing the particles having sizes of 150 μm or less in a smaller proportion is more suitable. Typically, the proportion is preferably 5 mass % or less, more preferably 3 mass % or less, and even more preferably 1 mass % or less. Further, the proportion of the particles having sizes of 150 μm to 850 μm is more preferably 95 mass % or more, more preferably 96 mass % or more, and even more preferably 98 mass % or more (with the upper limit being 100 mass %). The logarithmic standard deviation ($\sigma\zeta$) of the particle size distribution is in a range of preferably 0.2 to 0.5, more preferably 0.25 to 0.45, and even more preferably 0.30 to 0.40.

The particle size (e.g., a mass average particle diameter, the logarithmic standard deviation of the particle size distribution) of the water-absorbing resins or the like before the surface crosslinking is applied preferably to a water-absorbing resin obtained after surface crosslinking, and further to a water-absorbing agent composition, which is an end product. It is therefore preferable to subject the water-absorbing resins or the like to surface-crosslinking treatment such that the particle size before surface crosslinking can be maintained even after the surface crosslinking. In particular, it is more preferable to subject the water-absorbing resins or the like to surface-crosslinking treatment such that the mass average particle diameter (D50) before surface crosslinking and the proportion, before surface crosslinking, of the particles having sizes of 150 μm or less are maintained even after the surface crosslinking.

[Fine Powder Recycling Step]

The fine powder (e.g., the water-absorbing resins or the like having sizes of, for example, less than 150 μm) obtained in the classification step is recovered and recycled as appropriate. The fine powder is added to the aqueous monomer solution in the polymerization step. Alternatively, the fine powder is mixed with a large amount of water (in particular, water at a temperature of 50° C. to a boiling point) (such that a mass ratio between the fine powder and the water is 5:4 to 3:7) and the mixture is then added to the hydrogel obtained in the polymerization step. This makes it possible to reduce the amount of the water-absorbing resins or the like that fail to become end products and are therefore discarded.

[Surface-Crosslinking Step]

Surface-crosslinking the water-absorbing resin or the like that is obtained after undergoing each of the above steps and that has not been surface-crosslinked provides a water-absorbing resin or the like having been surface-crosslinked. Surface crosslinking is to provide, on the surface (near the surface: a depth of up to approximately several 10 μm from the surface of the water-absorbing resin or the like) of the water-absorbing resin or the like, a surface-crosslinked layer whose crosslink density is higher than the internal crosslink density. The surface crosslinking can be carried out, for example, by radical crosslinking or surface polymerization on the particle surface or by a surface-crosslinking reaction with use of a surface-crosslinking agent.

Examples of the surface-crosslinking agent include an oxazoline compound, a vinyl ether compound, an epoxy compound, an oxetane compound, a polyhydric alcohol compound, a polyamide polyamine-epihalo adduct, a hydroxyacrylamide compound, an oxazolidinone compound, a bis- or poly-oxazolidinone compound, a 2-oxotetrahydro-1,3-oxazolidine compound, an alkylene carbonate compound, and a polyvalent metal ion such as an aluminum salt. One surface-crosslinking agent or two or more surface-crosslinking agents of these surface-crosslinking agents is/are used. Alternatively, an organic acid and/or an inorganic acid, or the like may be used in combination with the surface-crosslinking agent. Further, the surface crosslinking can be carried out by polymerizing monomers on the surface of the water-absorbing resin or the like.

Examples of a more preferable method for the surface crosslinking include a method in which an epoxy compound and a polyamide polyamine-epihalo adduct are used as surface-crosslinking agents, a method in which a polyvalent metal ion such as an aluminum salt is used, a method in which an organic acid and/or an inorganic acid, or the like is/are used in combination with the surface-crosslinking agent, and the method of polymerizing monomers on the surface of the water-absorbing resin or the like. With these methods, it is possible to progress a surface-crosslinking reaction of the water-absorbing resin or the like at low temperature with the moisture content being maintained, and therefore obtain a water-absorbing agent composition excellent in various physical properties.

Specific examples of the surface-crosslinking agent include: a polyhydric alcohol compound such as (di, tri, tetra, poly)ethylene glycol, (di, poly)propylene glycol, 1,3-propanediol, 2,2,4-trimethyl-1,3-pentanediol, (poly)glycerin, 2-butene-1,4-diol, 1,3-butanediol, 1,4-butanediol, 1,5-pentanediol, 1,6-hexanediol, trimethylolpropane, diethanolamine or triethanolamine, pentaerythritol, or sorbitol; an epoxy compound such as (poly)ethylene glycol diglycidyl ether, (di, poly)glycerol polyglycidyl ether, (di, poly)propylene glycol diglycidyl ether, or glycidol; a polyvalent oxazoline compound such as 1,2-ethylenebisoxazoline; an alkylene carbonate compound such as 1,3-dioxolane-2-one; a polyvalent metal compound such as aluminum sulfate; and a polyamide polyamine-epihalohydrin adduct (e.g., Kymene 557LX, Kymene 557H, or Kymene plus available from Hercules Incorporated, WS4002, WS4020, WS4010, or WS4046 available from Seiko PMC Corporation).

The amount of the surface-crosslinking agent used is preferably 0.005 parts by mass to 10 parts by mass, more preferably 0.005 parts by mass to 5 parts by mass, and even more preferably 0.01 parts by mass to 3 parts by mass, relative to 100 parts by mass of the water-absorbing resin or the like before surface crosslinking. When the amount of the surface-crosslinking agent used is less than 0.005 parts by mass or exceeds 10 parts by mass, various physical properties of the water-absorbing agent composition can deteriorate.

As a solvent to be used for mixing the water-absorbing resin or the like and the surface-crosslinking agent, water is preferable. The amount of water used is preferably 1 part by mass to 10 parts by mass relative to 100 parts by mass of the water-absorbing resin or the like before surface crosslinking. This brings about sufficient permeation of the aqueous surface-crosslinking agent solution into the surface of the water-absorbing resin or the like. Accordingly, a multilayered, surface-crosslinked layer having an appropriate thickness and crosslink density is formed.

Alternatively, a hydrophilic organic solvent may be used as the solvent. Specific examples of the hydrophilic organic solvent include: lower alcohols such as methyl alcohol, ethyl alcohol, n-propyl alcohol, isopropyl alcohol, n-butyl alcohol, isobutyl alcohol, and t-butyl alcohol; a ketone such as acetone; ethers such as dioxane, tetrahydrofuran, and alkoxy polyethylene glycol; an amide such as N,N-dimethylformamide; a sulfoxide such as dimethyl sulfoxide. Although depending on the type, particle diameter, etc. of the water-absorbing resin or the like, the amount of hydrophilic organic solvent used is preferably 20 parts by mass or less and more preferably in a range of 0.1 parts by mass to 10 parts by mass, relative to 100 parts by mass of the water-absorbing resin or the like before surface crosslinking.

A method for mixing the water-absorbing resin or the like and the surface-crosslinking agent is not limited to any particular method, but is preferably a method of spraying or dropping, directly on the water-absorbing resin or the like, the surface-crosslinking agent dissolved in water and/or the hydrophilic organic solvent to mix the water-absorbing resin or the like and the surface-crosslinking agent.

A mixing apparatus for use in mixing the water-absorbing resin or the like and the surface-crosslinking agent preferably has a great mixing power so that the water-absorbing resin or the like and the surface-crosslinking agent are mixed together uniformly and reliably. Specific examples of the mixing apparatus include a cylindrical mixer, a double walled conical mixer, a V-shaped mixer, a ribbon mixer, a screw mixer, a flow-type rotary disk mixer, an airflow mixer, a double-arm kneader, an internal mixer, a pulverizing kneader, a rotary mixer, a screw extruder, a turbulizer.

After the water-absorbing resin or the like and the surface-crosslinking agent are mixed together, the mixture may be heated as appropriate so that a surface-crosslinking reaction progresses. A heating temperature is in a range of preferably 20° C. to 250° C., more preferably 30° C. to 200° C., and even more preferably 50° C. to 170° C. An embodiment of the present invention enables a reduction in, in particular, coloration, in relation to a surface-crosslinking reaction at 100° C. or higher. An embodiment of the present invention is effective in reducing coloration of the water-absorbing agent composition (water-absorbing resin) during a surface-crosslinking reaction at 100° C. to 250° C. Although depending on the heating temperature, a heating time is in a range of preferably 1 minute to 2 hours, more preferably 5 minutes to 1 hour, and even more preferably 10 minutes to 30 minutes. Examples of a suitable combination of the heating temperature and the heating time include: 70° C. to 120° C. and 3 minutes to 1 hour; 100° C. to 250° C. and 3 minutes to 1 hour; and 130° C. to 170° C. and 1 minute to 30 minutes. When undergoing surface crosslinking, the water-absorbing resin becomes more excellent in various physical properties including a fluid retention capacity under pressure (AAP).

Accordingly, a time when the surface-crosslinking step is ended refers to a point in time when a predetermined heating time elapses.

In order to obtain a water-absorbing agent composition excellent in various physical properties, it is preferable to carry out a surface-crosslinking reaction with the moisture content of the water-absorbing resin or the like before the surface crosslinking being kept in a range of preferably 3 mass % to 15 mass %, more preferably 4 mass % to 14 mass %, even more preferably 5 mass % to 13 mass %, and particularly preferably 6 mass % to 12 mass %. When the moisture content of the water-absorbing resin or the like before the surface crosslinking falls below 3 mass %, various physical properties of the water-absorbing agent composition can deteriorate. When the moisture content of the water-absorbing resin or the like before the surface crosslinking exceeds 15 mass %, handleability (fluidity) of the water-absorbing agent composition can decrease.

After the surface crosslinking, the water-absorbing resin or the like may be further dried as appropriate. In addition, after the surface crosslinking, the moisture content and various physical properties may be adjusted as appropriate by adding, for example, water and a further additive to the water-absorbing resin or the like. Examples of the further additive include a water-insoluble fine particle such as hydrophilic amorphous silica, a reducing agent, an antibacterial agent, a deodorant, a chelating agent, and a polyvalent metal compound. The amount of the further additive used is preferably 0.001 parts by mass to 20 parts by mass, more preferably 0.01 parts by mass to 10 parts by mass, and even more preferably 0.1 parts by mass to 5 parts by mass, relative to 100 parts by mass of the water-absorbing resin or the like after the surface crosslinking.

[Polysaccharide Adding Step]

A polysaccharide adding step is a step of adding a polysaccharide, in a period from the time when the polymerization step is started to the time when the surface-crosslinking step is ended, to at least one selected from the group consisting of the aqueous monomer solution, the hydrogel, the particulate hydrogel, the dried material, the pulverized substance of the dried material and the classified substance thereof, the water-absorbing resin before the surface crosslinking, and the water-absorbing resin after the surface crosslinking. The polysaccharide is added preferably at or after a time when the polymerization step is ended and more preferably at at least one time selected from the group consisting of a time before the gel-crushing step is started (and after the polymerization step is ended), a time when the gel-crushing step is started, a time during the gel-crushing step, and a time during a period from when the gel-crushing step is ended to when the drying is started. The polysaccharide is added particularly preferably at at least one time selected from the group consisting of the time before the gel-crushing step is started (and after the polymerization step is ended), the time when the gel-crushing step is started, and the time during the gel-crushing step.

A method for adding the polysaccharide is not limited to any particular method. The total amount of the polysaccharide may be added all at once or may be added in several portions. Further, the polysaccharide is preferably added in the form of a granule, powder, or the like.

When the polysaccharide is added at or after the time when the polymerization step is ended, the polysaccharide is delocalized on the surface of the water-absorbing resin particle. This causes the polysaccharide to be present in a part of the surface of the water-absorbing resin particle at a high concentration. A subsequent uniform mixing of the water-absorbing resin and the polysaccharide causes the water-absorbing resin and the polysaccharide to be present as if the surface of the water-absorbing resin particle is a sea and the polysaccharide is an island in the sea. Further, the polysaccharide is present on the surface of the water-absorbing resin particle at a high concentration. In other words, the polysaccharide content is greater in a surface-layer part of the water-absorbing agent composition than inside the water-absorbing agent composition. In a case where the polysaccharide is added at at least one time selected from the group consisting of the time before the gel-crushing step is started (and after the polymerization step is ended), the time when the gel-crushing step is started, and the time during the gel-crushing step, a method for the addition is not limited to any particular method, but kneading is a more preferable method so that uniform mixing is achieved. With such a method, in a case where, for example, the polysaccharide is starch, the starch becomes gelatinized (alpha-modified) with the water contained in the water-absorbing resin without undergoing a gelatinizing step, and is united (composited) with the water-absorbing resin. This causes the reducing agent to be uniformly dispersed in the composite resin of the polysaccharide and the water-absorbing resin that have been united together. It is therefore possible to reduce "coloration caused by heating during the production (mainly, a step of surface-crosslinking, at high temperature, the water-absorbing resin composition (base polymer composition) obtained after the drying step)!" observed in conventional water-absorbing agent compositions containing a polysaccharide.

The polysaccharide may be added such that the water-absorbing agent composition contains the polysaccharide in an amount of 10 mass % or more. The amount of the polysaccharide added is 10 mass % or more relative to a sum of the mass of the monomer composition used as a raw material in the polymerization step and the mass of the polysaccharide. The polysaccharide is contained in the water-absorbing agent composition in an amount of preferably 10 mass % or more and more preferably 20 mass % or more, with the total amount of the water-absorbing agent composition being 100 mass %. The polysaccharide content has an upper limit of preferably 50 mass % or less and more preferably 30 mass % or less.

When the polysaccharide is added at or after the time when the water-absorbing resin polymerization step is ended, the polysaccharide is delocalized on the surface of the water-absorbing resin. This causes the polysaccharide to be present in a part of the surface of the water-absorbing resin at a high concentration. In other words, the polysaccharide is present on the surface of the water-absorbing resin at a high concentration. Note that in a case where the polysaccharide is starch, using iodine (performing a starch-iodine reaction) makes it possible to easily confirm whether the water-absorbing resin, which is clear, and the polysaccharide, which becomes colored by the starch-iodine reaction, are present so as to be separated from each other.

[Reducing Agent Adding Step]

The reducing agent adding step is a step of adding the reducing agent to at least one selected from the group consisting of the aqueous monomer solution, the hydrogel, the dried material, the pulverized substance, and the water-absorbing resin, in a period from the time when the polymerization step is started to the time when the surface-crosslinking step is ended. The reducing agent is more preferably added in a period from the time when the polymerization step is ended to the time when the drying step (or the surface-crosslinking step) is started. The method for producing the water-absorbing resin composition in accordance with an embodiment of the present invention more preferably further includes the gel-crushing step between the polymerization step and the drying step, and the reducing agent is even more preferably added in a period from the time before the gel-crushing step is started (and after the polymerization step is ended) to the time before the surface-crosslinking step is started. The reducing agent is even more preferably added at at least one time selected from the group consisting of the time before the gel-crushing step is started (and after the polymerization step is ended), the time when the gel-crushing step is started, the time during the gel-crushing step, and the time during the period from when the gel-crushing step is ended to when the drying is started. In particular, it is preferable to add the reducing agent at at least one time selected from the group consisting of the time before the gel-crushing step is started (and after the polymerization step is ended), the time when the gel-crushing step is started, and the time during the gel-crushing step. It is most preferable to add the reducing agent before the gel-crushing step is started (and after the polymerization step is ended) and/or at the time when the gel-crushing step is started.

Further, it is particularly preferable to add both the polysaccharide and the reducing agent before the gel-crushing step is started (and after the polymerization step is ended) and/or at the time when the gel-crushing step is started. It is preferable that the method for producing the water-absorbing resin composition in accordance with an embodiment of the present invention also include a kneading step so that the polysaccharide and the reducing agent are uniformly mixed with the water-absorbing resin. With the kneading step being included, in a case where the polysaccharide is, for example, starch, the starch becomes gelatinized (alpha-modified) with the water contained in the water-absorbing resin without undergoing a gelatinizing step, and is united (composited) with the water-absorbing resin. This results in a form in which the reducing agent is uniformly dispersed in the composite resin of the polysaccharide and the water-absorbing resin that have been united together. With this form, it is possible to reduce "coloration caused by heating during the production (mainly, surface-crosslinking at high temperature) observed in conventional water-absorbing agent compositions containing a polysaccharide. Water-absorbing resin compositions containing an alpha-modified polysaccharide are likely to become colored by, in particular, undergoing a heating step. However, the present embodiment reduces such coloration. It is preferable to carry out the kneading step during the gel-crushing step and/or after the gel-crushing step. The gel-crushing step and the kneading step may be substantially concurrent.

After the kneading (only before the drying step) or after the gel-crushing, the solid content of a mixture containing the polysaccharide and the hydrogel has a concentration in a range of preferably 30 mass % to 80 mass % and more preferably 40 mass % to 70 mass %. In other words, the moisture content of the mixture is in a range of preferably 20 mass % to 70 mass % and more preferably 30 mass % to 60 mass %. In the kneading step or the gel-crushing step, the temperature of the mixture is in a range of preferably 50° C. to 100° C., more preferably 70° C. to 100° C., and even more preferably 90° C. to 100° C.

A method for adding the reducing agent is not limited to any particular method. The total amount of the reducing agent may be added all at once, or may be added in several portions. Further, it is preferable to add the reducing agent in a state of being dissolved in a solvent (preferably, water) to enable the reducing agent to be mixed more uniformly.

The amount of the reducing agent added is adjusted such that the water-absorbing agent composition contains the reducing agent in an amount of 10 ppm to 10000 ppm relative to the total amount of the water-absorbing agent composition. The amount of the reducing agent added is 10 ppm to 100000 ppm relative to a sum of the mass of the monomer composition used as a raw material in the polymerization step and the mass of the polysaccharide. The amount of the reducing agent added is more preferably 100 ppm to 80000 ppm, more preferably 1000 ppm to 50000 ppm, and most preferably 5000 ppm to 30000 ppm. A ratio between the amount of the polysaccharide added and the amount of the reducing agent added (the amount of the polysaccharide added the amount of the reducing agent added) is preferably from 99:1 to 80:20, more preferably 97:3 to 85:15, and even more preferably 95:5 to 90:10.

Adding the reducing agent to the water-absorbing resin makes it possible to prevent the water-absorbing agent composition to become colored due to heating during the production even when heat drying and surface-crosslinking treatment involving heating are carried out in the production. It is also possible to reduce the amount of residual monomers contained in the water-absorbing agent composition in the final product shipment stage.

[Difference from Conventional Art]

As disclosed in Patent Literatures 1 to 13, the water-absorbing resins in which a polysaccharide is used for part or whole of raw material thereof are known. However, such water-absorbing resins present the above problems because of low heat resistance of polysaccharides, in particular, low heat resistance of a polysaccharide mixed with a hydrogel. The inventors of the present invention conducted various studies to solve the above problems, and eventually found that a reducing agent is effective in preventing a polysaccharide (in particular, starch) mixed with a water-absorbing resin (in particular, hydrogel) from becoming colored during heating at high temperature, to bring the present invention to completion.

Note that there have been known techniques (for example, Patent Literatures 17 to 21) for adding a reducing agent to a water-absorbing resin in order to modify the water-absorbing resin (e.g., impart urine resistance to the water-absorbing resin (reduce gel deterioration caused by urine), reduce the amount of residual monomers of the water-absorbing resin, and prevent coloration of the water-absorbing resin during long-time storage). However, these techniques do not suggest the above effects at all.

Patent Literatures 1 to 13 on a water-absorbing resin in which a polysaccharide is used do not suggest at all addition of a reducing agent to the water-absorbing resin in which a polysaccharide is used, or contribution of the reducing agent to prevention of coloration, during heating at high temperature, of the water-absorbing resin in which a polysaccharide is used.

Patent Literatures 14 to 17 disclose gel-crushing of a hydrogel having been polymerized. However, Patent Literatures 14 to 17 also do not suggest at all addition of a reducing agent to the water-absorbing resin in which a polysaccharide is used, or contribution of the reducing agent to prevention of coloration, during heating at high temperature, of the water-absorbing resin in which a polysaccharide is used.

The water-absorbing agent composition in accordance with an embodiment of the present invention is produced without a decrease in productivity and is not colored due to heating (heat drying, surface-crosslinking treatment involving heating) during the production, even when a polysaccharide is used as a sustainable raw material for at least part of the water-absorbing agent composition. Polyacrylic acid (salt)-based water-absorbing resins contain a carboxylic acid (salt) group, and have mixed therein a free carboxylic acid and basic compound. Accordingly, when containing a polysaccharide such as starch, polyacrylic acid (salt)-based water-absorbing resins are easily colored due to heating during the production. In particular, in the step of surface-crosslinking, at high temperature, the water-absorbing resin composition (base polymer composition) obtained after the drying step, because the moisture content of the base polymer composition is low and the cooling property deteriorates accordingly, the water-absorbing resin composition easily becomes colored due to heating. With the conventional art, it is therefore difficult to solve the problem of coloration. However, with the water-absorbing agent composition in accordance with an embodiment of the present invention and the method, for producing a water-absorbing agent composition, in accordance with an embodiment of the present invention, it is possible to solve the problem of coloration that has been difficult to solve with the conventional art. The difference between the YI value of a resultant water-absorbing agent composition (end product) and the YI value of the base polymer composition, that is, $\Delta$YI value (YI value of water-absorbing agent composition–YI value of base polymer composition), is 20.0 or less, preferably 15.0 or less, more preferably 10.0 or less, and even more preferably 5.0 or less.

The water-absorbing agent composition can be used under high temperature conditions (under the condition of heating at 100° C. or higher).

[Various Physical Properties of Water-Absorbing Agent Composition]

To the water-absorbing agent composition obtained by carrying out each of the above steps, the above optional component may be added as appropriate.

The water-absorbing agent composition obtained by carrying out each of the above steps becomes colored due to heating during the production of the water-absorbing agent composition, and has a yellow index (YI value) measured by ASTM D1925 of 60 or less, more preferably 50 or less, and even more preferably 40 or less (the lower limit is 10).

The water-absorbing agent composition obtained by carrying out each of the above steps contains residual monomers in an amount of 1000 ppm or less, more preferably 700 ppm or less, and even more preferably 500 ppm or less (the lower limit is 1 ppm).

The water-absorbing agent composition obtained by carrying out each of the above steps has a fluid retention capacity under pressure (AAP0.3), measured under a pressure of 0.3 kPa, of 10 g/g or more, more preferably 12 g/g or more, and even more preferably 15 g/g or more. The upper limit of the fluid retention capacity under pressure measured under a pressure of 0.3 kPa (AAP0.3) is not limited to any particular value, but is 40 g/g or less, more preferably 35 g/g or less, and even more preferably 30 g/g or less.

The water-absorbing agent composition, in accordance with an embodiment of the present invention, obtained by carrying out each of the above steps can be suitably used in various water absorbent articles including hygienic materials (sanitary materials) such as disposable diapers, sanitary napkins, adult incontinence products (incontinence pads), and sheets for pets, agricultural and horticultural water retaining agents for soil, and industrial waterproofing agents.

EXAMPLES

The following description will discuss the present invention in greater detail on the basis of Examples and Comparative Examples. Note, however, that the present invention is not limited thereto in interpretation and that the present invention also encompasses in its scope any example derived from an appropriate combination of technical means disclosed in different Examples.

<Evaluation Method>

[CRC (Absorption Capacity without Load)]

A CRC (absorption capacity without load) was measured in conformity with NWSP 241.0.R2 (15). Specifically, a CRC (absorption capacity without load) (unit: g/g) was measured as follows: 0.2 g of the water-absorbing agent composition was placed in a nonwoven fabric bag and immersed in a large excess of a 0.9 mass % aqueous sodium chloride solution for 30 minutes so that the water-absorbing agent composition was freely swollen. The water-absorbing agent composition was then dehydrated by using a centrifugal separator (centrifugal force: 250 G), and the CRC (absorption capacity without load) (unit: g/g) thereof was measured.

[AAP (Absorption Capacity Under Load)]

An AAP (absorption capacity under load) was measured in conformity with NWSP 242.0.R2 (15) except that the load condition was changed from 0.7 psi to 0.3 psi. Specifically, with use of a large excess of 0.9 mass % aqueous sodium chloride solution, 0.9 g of the water-absorbing agent composition was swollen for 1 hour under a pressure of 2.07 kPa (21 g/cm$^2$, 0.3 psi), and the AAP (absorption capacity under load) (unit: g/g) thereof was then measured. Note that the result of the measurement under a load of 0.3 psi is denoted as AAP0.3.

[Degree of Coloration]

The degree of coloration of the water-absorbing agent composition was measured by the Hunter's Lab color system. As a measuring device, the spectrocolorimeter (SE-7700) available from NIPPON DENSHOKU INDUSTRIES Co., Ltd. was used. As a measurement condition, reflectance measurement was selected. The spectrocolorimeter is equipped with a container for powder and paste samples (30 mm in inner diameter, 12 mm in height), a standard white round plate No. 2 for powder and paste samples, and a 030 light-projecting pipe.

The container for powder and paste samples was filled with 5 g of the water-absorbing agent composition, and the L value, a value, b value, and YI value of the surface of the water-absorbing agent composition were measured at ambient temperature (20° C. to 25° C.) in a relative humidity 50 RH % atmosphere. A higher L value indicates being more bright, and a smaller YI value indicates being closer to white with lower coloration. By using the same measuring device and the same measurement method, the a and b values (chromaticity) that are other measures of the color of an object can also be measured. A smaller a value and a smaller b value each indicates being closer to white with lower coloration.

When the water-absorbing agent composition is the water-absorbing agent composition that is immediately after production or before factory shipment (typically), or the water-absorbing agent composition that has been stored at an ambient temperature of 30° C. or less and in a relative humidity 50% RH atmosphere and that is within one year after production, the color thereof is judged to remain unchanged over time, and this color is used as the degree of coloration of the water-absorbing agent composition.

[Residual Monomers]

The residual monomers were extracted by adding 1.0 g of the water-absorbing agent composition to 200 ml of a 0.9 mass % aqueous sodium chloride solution and then stirring the solution for one hour. Subsequently, the amount of residual monomers extracted in the aqueous sodium chloride solution (unit: ppm (by mass)) was measured by high performance liquid chromatography to be determined.

[Sodium Sulfite Content]

The amount of sodium sulfite contained in the water-absorbing agent composition was measured by extracting a soluble component from the water-absorbing agent composition, and then measuring, by high performance liquid chromatography, the amount of the soluble component extracted (unit: ppm (by mass)), and was thereby determined. Specifically, the determination was carried out by using the following method.

In Examples and Comparative Examples, the sodium sulfite content is equivalent to the amount of the reducing agent contained in the water-absorbing agent composition.

[Extraction of Soluble Component]

The water-absorbing agent composition was added in an amount of 0.1 g to 100 g of a 0.1 mass % aqueous formaldehyde solution, and the solution was then stirred at 500 rpm for one hour. The supernatant of an aqueous solution thereby obtained was filtered with use of a qualitative filter paper (No. 2, available from ADVANTEC), and a solution obtained by the filtration was used as an extracted solution.

[Quantitative Analysis by High Performance Liquid Chromatography]

Examples of the configuration of a high performance liquid chromatograph to be used for the determination of the sodium sulfite content include the following configuration.

Ion chromatography system: Dionex Integrion RFIC system

Column: Dionex IonPac AS11-HC, Dionex IonPac AG11-HC

First, sodium sulfite the amount of which is to be determined was dissolved in a 0.1 mass % aqueous formaldehyde solution so that an aqueous sodium sulfite solution having any concentration was prepared. This aqueous solution was analyzed with use of a high performance liquid chromatograph having the above configuration, and a calibration curve was created from the relationship between the peak area of a chromatogram thereby obtained and the concentration of the sodium sulfite. The peak detected in the high performance liquid chromatograph is a peak due to sulfite ions generated by ionization of the sodium sulfite. Accordingly, in the calculations, a mass conversion was made under the assumption that the sulfite ions are all sodium sulfite.

Subsequently, the extracted solution to be measured was analyzed with use of the high performance liquid chromatograph having the above configuration, and the sodium sulfite content of the water-absorbing agent composition was calculated from the relationship between the peak area of the obtained chromatogram and the calibration curve.

Note that, unless otherwise noted, raw material compounds, reagents, and solvents used in Examples and Comparative Examples were commercially available products (e.g., commercial products available from Nippon Shokubai Co., Ltd.).

Example 1

(Polymerization Solution (Aqueous Monomer Solution) Preparation Step)

In a 2-liter polypropylene vessel, 416.5 g of acrylic acid, 6.13 g of a solution of 10 mass % polyethyleneglycol diacrylate (molecular weight: 523) in acrylic acid (0.02 mol % relative to the acrylic acid) serving as the internal cross-linking agent, 1.29 g of a 2.0 mass % aqueous diethylen-etriamine pentaacetic acid/trisodium (DTPA-3Na) solution (0.96 mmol % relative to the acrylic acid) serving as the chelating agent, 352.6 g of 48.5 mass % aqueous sodium hydroxide solution, and 405.1 g of deionized water (ion-exchange water) were uniformly mixed together, so that an aqueous monomer solution was prepared.

(Production of Water-Absorbing Resin Composition)

While the aqueous monomer solution was being stirred with the solution temperature being kept at 77.5° C., 18.4 g of 4.5 mass % aqueous sodium persulfate solution was added as a polymerization initiator. Subsequently, the aqueous monomer solution was poured into a stainless steel vat-type container heated and adjusted, by a hot plate, to be 50° C. Three minutes after the polymerization reaction started, a hydrogel was taken out and cut into pieces such that each piece measures 60±5 g. Subsequently, all of the cut gels were put in a plastic bag (available from Okura Industrial Co., Ltd.: OK bag No. 18), and 76.7 g of 10 mass % aqueous sodium sulfite solution (18750 ppm relative to the solid content of the hydrogel. 15000 ppm relative to a sum of the mass of the monomer composition and the mass of the polysaccharide) was then fed into the bag as a reducing agent. The plastic bag was closed at the mouth immediately, and shaken for mixing until no water droplet adheres to the plastic bag.

Hydrogels obtained through the above operations were fed into a meat chopper (available from Hiraga factory, Co., Ltd.: type 32, plate pore diameter: 6.4 mm) at a rate of one hydrogel every 6 seconds while deionized water heated to 90° C. was also fed at a rate of 29 g per minute so that the hydrogel was crushed. A particulate hydrogel was thereby obtained.

In a plastic bag (available from Okura Industrial Co., Ltd.: OK bag No. 15), 787.0 g of this particulate hydrogel and 97.0 g of tapioca starch acetate BK-V (available from Tokai Denpun Co., Ltd.) as the polysaccharide (solid content: 90%, 25 mass % relative to the solid content of the hydrogel. Relative to a sum of the mass of the monomer composition and the mass of the polysaccharide, 20 mass % of the tapioca acetate starch was added. The tapioca starch acetate content of the water-absorbing agent composition became 20 mass %). The plastic bag was closed at the mouth immediately, and the plastic bag was then shaken for mixing so that the particulate hydrogel and the tapioca starch acetate were uniformly mixed. A mixture was thereby obtained.

The obtained mixture was fed into a 2.5-liter tabletop kneader (available from Koike iron works Co., Ltd.) heated and adjusted to be 90° C., and kneading and crushing were started. After the kneading speed was set to six-speed via a gearbox, 116.0 g of deionized water (ion-exchange water) was added to the kneaded mixture. Subsequently, the kneader was covered with a lid, and kneading was carried out for 15 minutes so that a kneaded gel mixed with starch was obtained.

On a 50-mesh metal gauze, 700.0 g of this kneaded gel mixed with starch was spread, and was then subjected to hot air drying at 170° C. for 45 minutes. A resultant dried material was pulverized with use of a roll mill (available from Inoguchi Giken Ltd.: WML type roll pulverizer) and sieved with use of a 600-μm mesh JIS sieve and a 300-μm mesh JIS sieve. A water-absorbing resin composition that is ground to have an uneven shape (base polymer composition) and that has a particle diameter of 300 μm to 600 μm was thereby obtained. The obtained base polymer composition was measured in terms of residual sodium sulfite, L value, a value, b value, and YI value. The measurement results are listed in Table 2.

To 100 parts by mass of the obtained base polymer composition, a surface-crosslinking agent solution consisting of 0.75 parts by mass of propylene glycol, 0.07 parts by mass of DENACOL EX-810 (available from Nagase Chem-teX Corporation), and 1.75 parts by mass of deionized water (ion-exchange water) was added. The base polymer composition and the surface-crosslinking agent solution were uniformly mixed, so that a mixture was obtained. Subsequently, surface-crosslinking treatment was performed on the mixture by performing heating treatment on the mixture at 100° C. for 40 minutes.

A water-absorbing resin composition thereby obtained that is after the surface crosslinking was pulverized to the extent of passing through an 850-μm mesh JIS standard sieve, so that a surface-crosslinked water-absorbing agent composition was obtained.

The obtained water-absorbing agent composition was measured in terms of CRC, AAP0.3, residual monomers, residual sodium sulfite, L value, a value, b value, and YI value. The measurement results are listed in Table 1. Further, the difference between the YI value of the obtained water-absorbing agent composition and the YI value of the base polymer composition, that is, ΔYI value (YI value of water-absorbing agent composition−YI value of base polymer composition), was calculated. The calculation result was listed in Table 2.

Example 2

A surface-crosslinked water-absorbing agent composition was obtained by carrying out the same operations as in Example 1 except that, unlike Example 1, surface-crosslinking agent solution was a uniformly mixed solution consisting of 100 parts by mass of the base polymer resin composition (base polymer composition), 0.4 parts by mass of ethylene carbonate, 0.7 parts by mass of propylene glycol, and 2.9 parts by mass of deionized water (ion-exchange water) and the temperature of the heating treatment was 210° C.

The obtained water-absorbing agent composition was measured in terms of CRC, AAP0.3, residual monomers, residual sodium sulfite, L value, a value, b value, and YI value. The measurement results are listed in Table 1. Further, the difference between the YI value of the obtained water-absorbing agent composition and the YI value of the base polymer composition, that is, ΔYI value (YI value of water-absorbing agent composition−YI value of base polymer composition), was calculated. The calculation result was listed in Table 2.

Example 3

A water-absorbing resin composition (base polymer composition) was obtained by carrying out the same operations as in Example 2 except that, unlike Example 2, 10 mass % aqueous sodium sulfite solution was not added to the hydro-gel.

Into 100 parts by mass of the obtained base polymer composition, 5 parts by mass of 20 mass % aqueous sodium sulfite solution (10000 ppm of a sum of the mass of the monomer composition and the mass of the polysaccharide) was uniformly mixed and a mixture thereby obtained was warmed at 60° C. for 30 minutes. A sodium sulfite-containing base polymer composition was thereby obtained. The obtained sodium sulfite-containing base polymer composition was measured in terms of residual sodium sulfite, L value, a value, b value, and YI value. The measurement results are listed in Table 2. Subsequently, the same surface crosslinking as in Example 2 was performed on the sodium sulfite-containing base polymer so that a surface-crosslinked water-absorbing agent composition was obtained. The obtained water-absorbing agent composition was measured in terms of CRC, AAP0.3, residual monomers, residual sodium sulfite, L value, a value, b value, and YI value. The measurement results are listed in Table 1. Further, the difference between the YI value of the obtained water-absorbing agent composition and the YI value of the base polymer composition, that is, ΔYI value (YI value of water-absorbing agent composition−YI value of base polymer composition), was calculated. The calculation result was indicated in Table 2.

Comparative Example 1

A water-absorbing agent composition was obtained by carrying out the same operations as in Example 1 except that, unlike Example 1, a 10 mass % aqueous sodium sulfite solution and tapioca starch acetate BK-V were not added to the hydrogel.

However, in the kneading by means of a tabletop kneader, the water content of a mixture to be fed into the tabletop kneader was adjusted to be equal to the water content of the mixture of Example 1. Specifically, the mixing of the hydrogel with 10 mass % aqueous sodium sulfite solution was not carried out, but the above-described cut hydrogels were fed into the meat chopper at a rate of one cur hydrogel every 6 seconds while the deionized water heated to 90° C. was also fed at a rate of 50 g per minute so that the hydrogel was crushed. A particulate hydrogel was thereby obtained. Further, the mixing of the particulate hydrogel with the tapioca starch acetate BK-V was not carried out, but 984 g of the particulate hydrogel and 16 g of deionized water were fed into the tabletop kneader and kneaded.

The obtained base polymer composition was measured in terms of residual sodium sulfite, L value, a value, b value, and YI value. The measurement results are listed in Table 2.

The obtained water-absorbing agent composition was measured in terms of CRC, AAP0.3, residual monomers, residual sodium sulfite, L value, a value, b value, and YI value. The measurement results are shown in Table 1. Further, the difference between the YI value of the obtained water-absorbing agent composition and the YI value of the base polymer composition, that is, ΔYI value (YI value of water-absorbing agent composition−YI value of base polymer composition), was calculated. The calculation result was shown in Table 2.

Comparative Example 2

A water-absorbing agent composition was obtained by carrying out the same operations as in Example 2 except that, unlike Example 2, a 10 mass % aqueous sodium sulfite solution was not added to the hydrogel.

Specifically, the mixing of the above-described cut gel with a 10 mass % aqueous sodium sulfite solution was not carried out, but the above-described cut gels were fed into the meat chopper at a rate of one cut gel every 6 seconds while the deionized water heated to 90° C. was also fed so that the cut gel was crushed. A particulate hydrogel was thereby obtained. However, the deionized water heated to 90° C. was fed at a rate of 50 g per minute, unlike Example 2, in which the rate was 29 g per minute.

The obtained base polymer composition was measured in terms of residual sodium sulfite, L value, a value, b value, and YI value. The measurement results are listed in Table 2. The obtained water-absorbing agent composition was measured in terms of CRC, AAP0.3, residual monomers, residual sodium sulfite, L value, a value, b value, and YI value. The measurement results are listed in Table 1. Further, the difference between the YI value of the obtained water-absorbing agent composition and the YI value of the base polymer composition, that is, ΔYI value (YI value of water-absorbing agent composition−YI value of base polymer composition), was calculated. The calculation result was shown in Table 2.

TABLE 1

| | Starch content (mass %) | Surface-crosslinking treatment temperature (° C.) | CRC (g/g) | AAP 0.3 (g/g) | Residual monomer (ppm) | Sodium sulfite content (ppm) | L value | a value | b value | YI value |
|---|---|---|---|---|---|---|---|---|---|---|
| Example 1 | 20 | 100 | 29.4 | 16.5 | 123 | 140 | 87.70 | −1.69 | 14.11 | 27.65 |
| Example 2 | 20 | 210 | 31.9 | 14.3 | 63 | 68 | 85.06 | −1.29 | 18.06 | 37.14 |
| Example 3 | 20 | 210 | 34.8 | 20.3 | 410 | 5268 | 83.38 | −0.73 | 20.48 | 43.58 |
| Comparative Example 1 | 0 | 100 | 40.1 | 27.1 | 397 | 0 | 86.70 | −0.62 | 10.80 | 22.00 |
| Comparative Example 2 | 20 | 210 | 31.1 | 26.0 | 1498 | 0 | 67.85 | 3.74 | 22.98 | 64.79 |

TABLE 2

| | Sodium sulfite content (ppm) | L value | a value | b value | YI value | Δ YI value |
|---|---|---|---|---|---|---|
| Example 1 Base polymer composition | 187 | 87.75 | −1.50 | 13.43 | 26.41 | 1.24 |
| Example 2 Base polymer composition | 187 | 87.75 | −1.50 | 13.43 | 26.41 | 10.73 |
| Example 3 Base polymer composition | 10000 | 84.64 | −0.90 | 18.65 | 38.92 | 4.66 |
| Comparative Example 1 Base polymer composition | 0 | 86.52 | −0.65 | 11.02 | 22.48 | −0.48 |
| Comparative Example 2 Base polymer composition | 0 | 81.30 | 0.74 | 19.58 | 43.99 | 20.80 |

As can be understood from Table 1, a water-absorbing agent composition which is the water-absorbing agent composition of Example 1 obtained by adding a polysaccharide (tapioca starch acetate) to a water-absorbing resin (particulate hydrogel) has a YI value approximately equal to the YI value of the water-absorbing agent composition of Comparative Example 1, which did not contain a polysaccharide. The water-absorbing agent compositions of Example 2 and Example 3 (end products after surface crosslinking) have lower YI values than the water-absorbing agent composition of Comparative Example 2 (end product after surface crosslinking) has. This indicates that the water-absorbing agent compositions of Examples 1 to 3 that contain a polysaccharide is reduced in coloration.

The water-absorbing resin compositions of Example 2 and Example 3 have smaller amounts of an increase in YI value (ΔYI value) from the YI value of the base polymer composition, which has not been surface-crosslinked (intermediate product), than the water-absorbing resin composition of Comparative Example 2 has. The same applies to Example 1. These indicates that addition of a reducing agent is effective in preventing coloration during high-temperature heating (hot air drying and surface-crosslinking treatment) during the production.

The present invention makes it possible to produce a water-absorbing resin containing a polysaccharide under the same conditions that are used in the production of conventional water-absorbing resins, by adding a reducing agent in a specific step during the production. This eliminates the need to invest in a new facility and lower drying temperature in order to prevent coloration, and thereby provides a water-absorbing resin that is produced with high productivity and is excellent in physical properties.

INDUSTRIAL APPLICABILITY

The water-absorbing agent composition in accordance with an embodiment of the present invention can be suitably used in various water absorbent articles including hygienic materials (sanitary materials) such as disposable diapers, sanitary napkins, adult incontinence products (incontinence pads), and sheets for pets, agricultural and horticultural water retaining agents for soil, and industrial waterproofing agents.

The invention claimed is:

1. A water-absorbing agent composition comprising a polyacrylic acid (salt)-based water-absorbing resin, a polysaccharide, and a reducing agent,
    said water-absorbing agent composition being surface-crosslinked,
    said water-absorbing agent composition containing said polysaccharide in an amount of 10 mass % or more and containing said reducing agent in an amount of 10 ppm to 10000 ppm, and said water-absorbing agent composition having a degree of coloration (YI value) of 60 or less,
    the polysaccharide being present in a part of a surface of said water-absorbing agent composition at a high concentration.

2. The water-absorbing agent composition according to claim 1, wherein said reducing agent contains one or more compounds selected from the group consisting of an inorganic compound containing a sulfur atom, an organic compound containing a sulfur atom, and an inorganic compound containing a phosphorus atom.

3. The water-absorbing agent composition according to claim 1, wherein said reducing agent is sodium hydrogen sulfite and/or sodium sulfite.

4. The water-absorbing agent composition according to claim 1, wherein said polysaccharide is starch and/or a modified starch.

5. The water-absorbing agent composition according to claim 1, wherein said water-absorbing agent composition contains residual monomers in an amount of 1000 ppm or less.

6. The water-absorbing agent composition according to claim 1, wherein said water-absorbing agent composition has a fluid retention capacity under pressure (AAP0.3), measured under a pressure of 0.3 kPa, of 10 g/g or more.

7. A method for producing a water-absorbing agent composition including a polyacrylic acid (salt)-based water-absorbing resin, a polysaccharide, and a reducing agent, said method comprising;
    a polymerization step, a drying step, and a surface-crosslinking step in this order in a production process of said water-absorbing agent composition,
    at any stage from a time when said polymerization step is started to a time when said surface-crosslinking step is ended, said polysaccharide and said reducing agent being added in an amount of 10 mass % or more and in an amount of 10 ppm to 100000 ppm, respectively, relative to a sum of the mass of a monomer composition introduced in said polymerization step and the mass of said polysaccharide, and
    wherein said polysaccharide is added at or after a time when said polymerization step is ended.

8. The method according to claim 7, further comprising a gel-crushing step between said polymerization step and said drying step,
    said polysaccharide being added at at least one time selected from the group consisting of a time before said gel-crushing step is started (and after said polymerization step is ended, a time when said gel-crushing step is started, and a time during said gel-crushing step.

9. The method according to claim 7, wherein said reducing agent is added in a period from a time when said polymerization step is ended to a time when said drying step is started.

10. The method according to claim 7, further comprising a gel-crushing step between said polymerization step and said drying step, said reducing agent being added between a time before said gel-crushing step is started and after said polymerization step is ended) and a time before said surface-crosslinking step is started.

11. The method according to claim 7, further comprising a gel-crushing step between said polymerization step and said drying step, said reducing agent being added before said gel-crushing step is started (and after said polymerization step is ended and/or at a time when said gel-crushing step is started.

12. The method according to claim 7, further comprising a gel-crushing step between said polymerization step and said drying step, said polysaccharide being added at at least one time selected from the group consisting of a time before said gel-crushing step is started and after said polymerization step is ended, a time when said gel-crushing step is started, and a time during said gel-crushing step, and said reducing agent being added between said time before said gel-crushing step is started (and after said polymerization step is ended and a time before said surface-crosslinking step is started.

13. The method according to claim 7, wherein said surface-crosslinking step includes a surface-crosslinking reaction at 100° C. to 250° C.

14. A water-absorbing agent composition produced by said method according to claim 7.

* * * * *